United States Patent
Cushner et al.

(10) Patent No.: US 10,966,593 B2
(45) Date of Patent: Apr. 6, 2021

(54) IN-LINE GAS ADAPTOR FOR ENDOSCOPIC APPARATUS

(71) Applicant: UNITED STATES ENDOSCOPY GROUP, INC., Mentor, OH (US)

(72) Inventors: Jeffrey B. Cushner, Woodmere, NY (US); Kenneth W. Locke, Sandy Hook, CT (US); Christopher R. Stebbins, Huntington Station, NY (US); Kenneth E. Wolcott, Centerport, NY (US)

(73) Assignee: UNITED STATES ENDOSCOPY GROUP, INC., Mentor, OH (US)

( * ) Notice: Subject to any disclaimer, the term of this patent is extended or adjusted under 35 U.S.C. 154(b) by 92 days.

(21) Appl. No.: 13/873,598

(22) Filed: Apr. 30, 2013

(65) Prior Publication Data
US 2013/0237761 A1  Sep. 12, 2013

Related U.S. Application Data

(63) Continuation of application No. 12/869,265, filed on Aug. 26, 2010, now Pat. No. 8,454,498.
(Continued)

(51) Int. Cl.
*A61B 1/00* (2006.01)
*A61M 39/10* (2006.01)

(52) U.S. Cl.
CPC ...... *A61B 1/00119* (2013.01); *A61B 1/00068* (2013.01); *A61B 1/00128* (2013.01);
(Continued)

(58) Field of Classification Search
CPC ............ A61B 1/00119; A61B 1/00128; A61B 1/00121; A61B 1/12; A61B 1/125; A61M 39/10
(Continued)

(56) References Cited

U.S. PATENT DOCUMENTS 1,034,170 A   7/1912   Vanier
D189,383 S   11/1960   Macomber
(Continued)

FOREIGN PATENT DOCUMENTS

DE   33 24 730 A1   1/1984
EP    0075153 A2   3/1983
(Continued)

OTHER PUBLICATIONS

Office Action for Japanese Application No. 2012-526984; dated May 31, 2013.
(Continued)

*Primary Examiner* — Alexandra L Newton
*Assistant Examiner* — Rynae Boler
(74) *Attorney, Agent, or Firm* — Calfee Halter & Griswold LLP

(57) ABSTRACT

The present invention provides an adaptor that is suitable for attachment to an endoscopic device for delivery of a secondary gas. The adaptor generally comprises an adaptor body with first and second fluid transport components and can include a gas inlet on one of the fluid transport components suitable for attachment to a secondary gas source. A sealing member can be included to prevent leakage of any fluid (e.g., liquid or gas) that is transported through channels extending through the fluid transport components. The adaptor may be used in endoscopy methods and is particularly useful for adding a secondary gas source in an endoscopy procedure.

21 Claims, 19 Drawing Sheets

Related U.S. Application Data

(60) Provisional application No. 61/238,332, filed on Aug. 31, 2009.

(52) U.S. Cl.
CPC ............ *A61M 39/10* (2013.01); *A61M 39/105* (2013.01); *A61M 2039/1077* (2013.01); *A61M 2039/1083* (2013.01); *A61M 2039/1088* (2013.01)

(58) Field of Classification Search
USPC ............ 600/154, 156, 158, 159; 604/164.02, 604/533, 537–539
See application file for complete search history.

(56) References Cited

U.S. PATENT DOCUMENTS

| | | | |
|---|---|---|---|
| 3,135,412 A | 6/1964 | Cornelius | |
| 3,222,135 A | 12/1965 | Ashmead | |
| 3,390,897 A | 7/1968 | Buell | |
| D227,558 S | 7/1973 | Matthews, Jr. | |
| 4,108,172 A | 8/1978 | Moore, Jr. | |
| 4,258,721 A | 3/1981 | Parent et al. | |
| 4,261,343 A | 4/1981 | Ouchi et al. | |
| 4,261,345 A | 4/1981 | Yamaguchi | |
| 4,262,671 A | 4/1981 | Kersten | |
| 4,311,134 A | 1/1982 | Mitsui et al. | |
| 4,325,362 A | 4/1982 | Ouchi et al. | |
| 4,350,647 A | 9/1982 | De la Cruz | |
| D267,743 S | 1/1983 | Cummingham et al. | |
| D271,618 S | 11/1983 | Nishigaki | |
| 4,416,268 A * | 11/1983 | Hagino .............. | A61B 1/00119 600/132 |
| 4,464,316 A | 8/1984 | Michaels | |
| 4,474,574 A | 10/1984 | Wolfe et al. | |
| 4,489,712 A | 12/1984 | Ohshima | |
| 4,494,252 A | 1/1985 | Chaoui | |
| D280,206 S | 8/1985 | Ishii | |
| 4,538,593 A | 9/1985 | Ishii | |
| 4,539,586 A | 9/1985 | Danna et al. | |
| 4,548,197 A | 10/1985 | Kinoshita | |
| 4,550,716 A | 11/1985 | Kinoshita | |
| 4,552,130 A | 11/1985 | Kinoshita | |
| 4,637,378 A * | 1/1987 | Sasa .............................. | 600/155 |
| 4,667,655 A | 5/1987 | Ogiu et al. | |
| 4,691,701 A | 9/1987 | Williams | |
| 4,701,159 A | 10/1987 | Brown et al. | |
| 4,708,126 A | 11/1987 | Toda et al. | |
| 4,748,970 A | 6/1988 | Nakajima | |
| 4,760,838 A | 8/1988 | Fukuda | |
| D299,538 S | 1/1989 | Balding et al. | |
| 4,800,869 A | 1/1989 | Nakajima | |
| 4,844,052 A | 7/1989 | Iwakoshi et al. | |
| 4,901,142 A | 2/1990 | Ikuno et al. | |
| 4,905,852 A | 3/1990 | Zumbuhl | |
| 4,968,309 A | 11/1990 | Andersson | |
| 5,027,791 A | 7/1991 | Takahashi | |
| 5,054,481 A | 10/1991 | Shin | |
| 5,083,549 A | 1/1992 | Cho et al. | |
| 5,125,915 A | 6/1992 | Berry et al. | |
| 5,133,336 A * | 7/1992 | Savitt et al. .................. | 600/132 |
| 5,163,576 A | 11/1992 | Galer | |
| 5,192,439 A | 3/1993 | Roth et al. | |
| 5,297,537 A | 3/1994 | Savitt et al. | |
| 5,309,906 A | 5/1994 | LaBombard | |
| 5,343,855 A | 9/1994 | Iida et al. | |
| 5,402,770 A | 4/1995 | Iida et al. | |
| 5,607,391 A | 3/1997 | Klinger et al. | |
| 5,630,795 A | 5/1997 | Kuramoto et al. | |
| 5,634,880 A | 6/1997 | Feldman et al. | |
| 5,697,888 A | 12/1997 | Kobayashi et al. | |
| D392,046 S | 3/1998 | Niedospial, Jr. | |
| 5,810,718 A | 9/1998 | Akiba et al. | |
| 5,830,128 A | 11/1998 | Tanaka | |
| 5,871,111 A | 2/1999 | Pfefferkorn et al. | |
| 5,902,264 A | 5/1999 | Toso et al. | |
| 5,902,413 A | 5/1999 | Puszko et al. | |
| 6,189,870 B1 | 2/2001 | Withall | |
| 6,210,322 B1 | 4/2001 | Byrne | |
| 6,220,482 B1 | 4/2001 | Simmel et al. | |
| 6,391,000 B1 | 5/2002 | Belikan et al. | |
| 6,485,412 B1 | 11/2002 | Byrne | |
| 6,485,684 B1 | 11/2002 | Mapson et al. | |
| 6,558,317 B2 | 5/2003 | Takahashi et al. | |
| 6,575,160 B1 | 6/2003 | Volgyesi | |
| 6,575,946 B2 | 6/2003 | Sealfon | |
| 6,702,738 B2 | 3/2004 | Ito | |
| 6,764,442 B2 | 7/2004 | Ota et al. | |
| 6,840,902 B2 | 1/2005 | Sano et al. | |
| 6,855,109 B2 * | 2/2005 | Obata ..................... | A61B 1/12 600/101 |
| 6,860,516 B2 | 3/2005 | Ouchi et al. | |
| 6,984,204 B2 | 1/2006 | Akiba | |
| 7,066,177 B2 | 6/2006 | Pittaway et al. | |
| 7,347,355 B2 | 3/2008 | Sato et al. | |
| 7,399,273 B2 | 7/2008 | Moriyama et al. | |
| 7,568,735 B2 | 8/2009 | Akiba | |
| 7,578,294 B2 | 8/2009 | Pierro et al. | |
| 7,582,056 B2 | 9/2009 | Noguchi et al. | |
| 7,597,662 B2 | 10/2009 | Litscher et al. | |
| D612,496 S | 3/2010 | Bennison | |
| 7,678,044 B2 | 3/2010 | Fujikura | |
| 7,766,898 B2 | 8/2010 | Mottola et al. | |
| 7,806,850 B2 | 10/2010 | Williams, Jr. et al. | |
| 7,824,329 B2 | 11/2010 | Aizenfeld et al. | |
| 7,837,769 B2 | 11/2010 | Lahr | |
| 7,892,223 B2 | 2/2011 | Geiselhart | |
| 7,901,350 B2 | 3/2011 | Yamazaki | |
| 7,914,519 B2 | 3/2011 | Moran et al. | |
| D639,940 S | 6/2011 | Cushner et al. | |
| 7,963,914 B2 | 6/2011 | Uchimura et al. | |
| D652,923 S | 1/2012 | Kennedy et al. | |
| 8,152,716 B2 | 4/2012 | Aizenfeld et al. | |
| 8,454,498 B2 | 6/2013 | Cushner et al. | |
| 8,454,499 B2 | 6/2013 | Cushner et al. | |
| 2001/0044594 A1 | 11/2001 | Martin et al. | |
| 2003/0032860 A1 | 2/2003 | Avni et al. | |
| 2003/0032862 A1 | 2/2003 | Ota et al. | |
| 2003/0045779 A1 | 3/2003 | Ito | |
| 2003/0073971 A1 | 4/2003 | Saker | |
| 2004/0153047 A1 | 8/2004 | Blank et al. | |
| 2004/0199052 A1 | 10/2004 | Banik et al. | |
| 2004/0260151 A1 | 12/2004 | Akiba | |
| 2005/0263480 A1 | 12/2005 | Smolko et al. | |
| 2006/0052663 A1 | 3/2006 | Koitabashi | |
| 2006/0052665 A1 | 3/2006 | Aizenfeld et al. | |
| 2006/0068360 A1 | 3/2006 | Boulais | |
| 2006/0106285 A1 | 5/2006 | Boulais et al. | |
| 2006/0135851 A1 | 6/2006 | Yamazaki | |
| 2006/0178648 A1 | 8/2006 | Barron et al. | |
| 2006/0229498 A1 | 10/2006 | Kohno | |
| 2006/0241348 A1 | 10/2006 | Kohno | |
| 2006/0266423 A1 | 11/2006 | Akiba et al. | |
| 2006/0276689 A1 | 12/2006 | Litscher et al. | |
| 2006/0293562 A1 | 12/2006 | Uchimura et al. | |
| 2007/0043261 A1 | 2/2007 | Watanabe et al. | |
| 2007/0043262 A1 | 2/2007 | Levy et al. | |
| 2007/0066866 A1* | 3/2007 | Noguchi .............. | A61B 1/0005 600/102 |
| 2007/0145738 A1 | 6/2007 | Akiba | |
| 2007/0129705 A1 | 7/2007 | Trombley, III et al. | |
| 2007/0225566 A1 | 9/2007 | Kawanishi | |
| 2007/0238929 A1* | 10/2007 | Aizenfeld .............. | A61B 1/015 600/158 |
| 2007/0244363 A1 | 10/2007 | Sano et al. | |
| 2008/0132763 A1 | 6/2008 | Isaacson | |
| 2008/0154095 A1 | 6/2008 | Stubkjaer et al. | |
| 2008/0214895 A1 | 9/2008 | Campos | |
| 2008/0269560 A1 | 10/2008 | Ito et al. | |
| 2009/0032533 A1 | 2/2009 | Kessell et al. | |
| 2009/0101562 A1* | 4/2009 | Newton .................. | A61M 3/02 210/232 |
| 2009/0143719 A1 | 6/2009 | Loori et al. | |

(56) References Cited

U.S. PATENT DOCUMENTS

| | | | |
|---|---|---|---|
| 2009/0188919 | A1 | 7/2009 | Takanohashi |
| 2009/0209822 | A1 | 8/2009 | Ikeda |
| 2009/0260629 | A1 | 10/2009 | Yee et al. |
| 2009/0264705 | A1 | 10/2009 | Cushner et al. |
| 2009/0266357 | A1 | 10/2009 | Varis et al. |
| 2009/0299134 | A1* | 12/2009 | Bettocchi ............... A61B 1/12 600/104 |
| 2010/0022834 | A1 | 1/2010 | Noda et al. |
| 2011/0174822 | A1 | 7/2011 | Gasser et al. |
| 2011/0263939 | A1 | 10/2011 | Kaye et al. |
| 2011/0275945 | A1 | 11/2011 | Karla et al. |
| 2012/0209062 | A1 | 8/2012 | Qiao |
| 2013/0245377 | A1 | 9/2013 | Cushner et al. |
| 2014/0316204 | A1 | 10/2014 | Ofir et al. |
| 2014/0316205 | A1 | 10/2014 | Bendele et al. |
| 2015/0080661 | A1 | 3/2015 | Kaye et al. |
| 2015/0297063 | A1 | 10/2015 | Wolcott et al. |

FOREIGN PATENT DOCUMENTS

| | | |
|---|---|---|
| EP | 0082950 A2 | 7/1983 |
| EP | 0361086 A1 | 4/1990 |
| EP | 0437229 A1 | 7/1991 |
| EP | 2 428 157 A1 | 3/2012 |
| JP | 62-125501 U | 8/1987 |
| JP | 1099558 A | 4/1989 |
| JP | H01280437 A | 11/1989 |
| JP | 5168587 A | 7/1993 |
| JP | 5220103 A | 8/1993 |
| JP | 5337074 A | 12/1993 |
| JP | 7-9301 U | 2/1995 |
| JP | 8106052 A | 4/1996 |
| JP | 08112251 A | 5/1996 |
| JP | 9164113 A | 6/1997 |
| JP | 10099265 A | 4/1998 |
| JP | 10-276963 A | 10/1998 |
| JP | 2001299685 A | 10/2001 |
| JP | 2002 177205 A | 6/2002 |
| JP | 2003-024266 A | 1/2003 |
| JP | 2003-070731 A | 3/2003 |
| JP | 2003111721 A | 4/2003 |
| JP | 2003-339619 A | 12/2003 |
| JP | 2004-147833 A | 5/2004 |
| JP | 2004-242877 A | 9/2004 |
| JP | 2004-305758 A | 11/2004 |
| JP | 2005-021710 A | 1/2005 |
| JP | 2005-245668 A | 9/2005 |
| JP | 2005-304780 A | 11/2005 |
| JP | 2006-042874 A | 2/2006 |
| JP | 2006-110215 A | 4/2006 |
| JP | 2006-116000 A | 5/2006 |
| JP | 2006-167064 A | 6/2006 |
| JP | 2006-280536 A | 10/2006 |
| JP | 2007-089623 A | 4/2007 |
| JP | 2007-252834 A | 10/2007 |
| JP | 2007-313047 A | 12/2007 |
| JP | 2008-029742 A | 2/2008 |
| JP | 2010-057728 A | 3/2010 |
| WO | WO 93/14688 A1 | 8/1993 |
| WO | WO 2006/109351 A1 | 10/2006 |
| WO | WO-2008/122969 A1 | 10/2008 |
| WO | WO 2009/129302 A1 | 10/2009 |

OTHER PUBLICATIONS

Communication Pursuant to Article 94(3) EPC for Application No. 10 749 572.3; dated Nov. 29, 2013.
Office Action for U.S. Appl. No. 13/874,568 dated Jul. 30, 2015.
Office Action for Canadian Application No. 2,772,341 dated Nov. 3, 2014.
Endoscope Channel Guide, Evis™ 40/140/240 & Exera™ 160-Series GI Endoscopes, Olympus America, Inc. (2003), 1 page.
International Search Report and Written Opinion for Application No. PCT/US2009/040655 dated Jun. 29, 2009.
International Preliminary Report on Patentability for Application No. PCT/US2009/040655 dated Oct. 19, 2010.
International Search Report for Application No. PCT/US2014/025948 dated Jul. 29, 2014.
International Search Report and Written Opinion for Application No. PCT/US2013/032005 dated Jun. 18, 2013.
Office Action for Chinese Application No. 201080046225.0 dated May 4, 2014.
Office Action for Chinese Application No. 200980113305.0 dated Nov. 16, 2011.
Notice of Decision of Granting Patent for Application No. 200980113305.0 dated Apr. 9, 2012.
Communication for European Patent Application No. 09 731 691.3, dated Dec. 5, 2011, 4 pages.
Office Action for European Application No. 09 731 691.3 dated Oct. 28, 2014.
Office Action for Japanese Patent Application No. 2011-505165 dated Sep. 21, 2012.
Office Action for U.S. Appl. No. 29/335,421 dated Dec. 7, 2010.
Notice of Allowance for Design U.S. Appl. No. 29/335,421 dated Feb. 10, 2011.
Office Action for U.S. Appl. No. 12/424,211 dated Apr. 23, 2012.
Office Action for U.S. Appl. No. 12/424,211 dated Oct. 5, 2012.
Office Action for U.S. Appl. No. 12/424,211 dated Dec. 4, 2013.
Notice of Allowance for U.S. Appl. No. 12/424,211 dated Mar. 28, 2014.
Notice of Allowance for U.S. Appl. No. 12/869,265 dated Feb. 4, 2013.
Notice of Allowance for U.S. Appl. No. 12/881,683 dated Jul. 2, 2013.
Communication Pursuant to Article 94(3) EPC from European Application No. 10749572.3 dated Jun. 14, 2016.
International Search Report and Written Opinion from PCT/US2017/025655 dated Sep. 12, 2017.
International Search Report and Written Opinion from International Application No. PCT/US2010/048578, dated Jan. 28, 2011.
International Search Report and Written Opinion for Appl. No. PCT/US2010/046805 dated Dec. 7, 2010.
International Preliminary Report on Patentability for Application No. PCT/US2010/046805 dated Mar. 15, 2012.
Written Opinion for Application No. PCT/US2010/046805 (undated).
U.S. Appl. No. 12/869,265, filed Aug. 26, 2010; In re: Cushner et al.; entitled *In-Line Gas Adaptor for Endoscopic Apparatus*.
Office Action for U.S. Appl. No. 12/869,265 dated Aug. 16, 2012.
Office Action for U.S. Appl. No. 12/881,683 dated Aug. 22, 2012.
E-Scope (endoscope sales/services), e-Scope, LLC Brochure, dated Jan. 16, 2008, 2 pages.
Periphery Accessories Programme, PENTAX Brochure, (undated), 20 pages.
Office Action for U.S. Appl. No. 13/874,568 dated Mar. 26, 2015.
Notice of Allowance for U.S. Appl. No. 14/301,747 dated Mar. 31, 2015.

* cited by examiner

IN-LINE GAS ADAPTOR FOR ENDOSCOPIC APPARATUS

CROSS-REFERENCE TO RELATED APPLICATIONS

This application is a continuation of U.S. application Ser. No. 12/869,265, filed Aug. 26, 2010, which claims priority to U.S. Provisional Application No. 61/238,332, filed Aug. 31, 2009, each of which is incorporated herein by reference in its entirety.

FIELD OF THE INVENTION

The present application is directed to devices used in surgical procedures, such as endoscopic procedures, and more particularly to a device that can be used to connect a secondary gas source to an apparatus, such as an endoscopic apparatus.

BACKGROUND

Many invasive medical procedures that previously required major surgery are now performed using endoscopic instruments. Such instruments can provide an internal view of particular body parts, organs, or passages without requiring invasive surgery. Generally, an endoscopic instrument may include one or more channels through which miniaturized, flexible instruments can be inserted and advanced. The endoscope typically includes an elongated flexible cable equipped at one end with an eyepiece or other viewing means and at the other end with an optical head. Only the head is directly and externally connected to the instrument. The cable transmits images or image-producing signals from the illuminated operative site to the viewing means to provide the instrument operator with full vision of the actions being performed at the instrument's working end. A coherent optic bundle extends from the head and through the flexible cable through the eyepiece for providing the surgeon with visual confirmation of the instrument's tip or jaw action. The illuminating means may take the form of a light-transmitting waveguide extending through the cable to illuminate the operative area. The waveguide is connected at its proximal end to a suitable high-intensity light source.

The cable of an endoscope also provides a flow passage for the delivery of fluid (e.g., liquid or gas) for irrigation or other purposes. Typically, the flow passage and the illuminating means are disposed on opposite sides of the coherent image-transmitting waveguide. In conventional practice, it is necessary to provide a flow of sterile water across the optic head to prevent the buildup of materials (e.g., surgical debris and body fluids) on the optic head. This flow of water operates, in a sense, like a windshield wiper/washer assembly.

In common designs, an endoscopic instrument typically has a control body which is connected by a light guide tube to a light guide connector, which actually can include a plurality of connectors that can suitably receive various fittings. For example, the light guide connector can include a connector orifice that receives a grounding lug, a suction port, an air inlet, and a water inlet. As such, the air and water are delivered through the light guide connector, through the light guide tube and into the control body. Alternatively, the control body can also include a water port so as to allow water to be directly provided to the control body. Suitable valves are provided on the control body so as to control the flow of water through the control body and over the optic head of the instrument.

For example, FIG. 1 illustrates an endoscope system that is unmodified (i.e., includes no secondary gas supply means). The endoscope is shown to include a shaft (insertion tube) connected to a control body that includes a biopsy port, air-water and suction valves, and angulation controls. The control body is connected to an umbilical (light guide connecting tube) that further connects to an electrical pin unit, which is directly connected to a light source and is connected via a video connection lead (and plug) to a video processor. The image produced by the endoscope is transmitted via a fiber optic bundle, or electronically from a charge-coupled device (CCD) chip. FIG. 1 illustrates a video monitor and attached keyboard for viewing images and inputting commands. The electrical pin unit includes a port for a water bottle connector that connects to a water bottle for providing irrigation.

The somewhat complex internal anatomy of the endoscope is further illustrated in FIG. 2, which shows a detailed view of the endoscope from FIG. 1. As seen in FIG. 2, the shaft incorporates an instrumentation channel extending from the entry biopsy port to the tip of the instrument. Channel sizes can vary from about 1 to 5 mm. Again, the endoscope includes no means for a secondary gas supply.

As seen in FIG. 1, the known practice has been to use a water bottle with a cap having a tube running therethrough. The tube typically has a fitting at the end distal to the bottle to allow for connection to the air/water connection port of the light guide connector (of the electrical pin unit, as illustrated in FIG. 1) or to the port on the endoscope control body. Typically, the tube connecting the water bottle to the endoscope is formed of an inner tube and an outer tube. The outer tube extends into the water bottle and is connected to the cap of the water bottle. In normal practice, air is delivered through the area between the inner tube and the outer tube so as to pressurize the interior of the water bottle and force water to flow through the tube and into the endoscope at a desired rate.

The known endoscopy assemblies have various limitations in relation to the provision of a gas source. For example, ambient air is often pumped into the system to charge the water bottle. It can be desirable, however, to use a secondary gas source instead of ambient air. Known devices allowing for substitution with a secondary gas source are excessively expensive. Moreover, known devices suffer problems associated with disinfection after each use. In practice, after usage, any fittings associated with the endoscopy device are sterilized, such as by glutaraldehyde disinfection and/or autoclaving. This creates a considerable expense to the hospital including the considerable labor expense associated with the disinfection of various parts and fittings. It also has not typically been feasible to simply dispose of various endoscopy fittings after a single use because of the previously noted expense associated with such parts.

Still further, the provision of a secondary gas source is complicated in that known endoscopy devices do not have universal, standardized connections. For example, the three main manufacturers of endoscopy devices (Olympus Optical Company, Ltd., Fujifilm Medical Systems, or its subsidiary, Fujinon Inc., and Hoya Corporation, or its subsidiary, Pentax) each manufacture devices with an endoscope body that is universal to its own line of products but which is not suited for interchanging of parts between brands. Specifically, water bottle connectors for each manufacturer connect to the endoscope body via a different type of connection. Thus, there remains a need in the art for adaptors that allow for provision of a secondary gas in a manner that is economical and easy to use.

SUMMARY OF THE INVENTION

The present invention provides adaptors to improve the ease of provision and use of a secondary gas source in endoscopy. The inventive adaptors can be designed and shaped to function with endoscopic devices generally or may be designed and shaped to function with endoscopic devices having a particular structure unique to a single manufacturer of endoscopic devices. In light of their economical nature (and option for disposable, single use), the inventive adaptors allow for provision of a secondary gas in an endoscopy procedure without the requirement of costly, specialized equipment, such as a water bottle with a specially designed cap or a re-usable adaptor that has a much greater initial cost and must be sterilized between uses. These and other benefits of the present invention are more fully described herein.

In certain embodiments, the present invention provides adaptors that can be used with endoscopic devices. In particular, the adaptors can allow for the provision of a secondary gas to the endoscopic device via in-line placement between the endoscopic device and a water source connector.

In one embodiment, an adaptor according to the invention can comprise an adaptor body having a particular structure. For example, the adaptor body can comprise a first fluid transport component that is connected to a second fluid transport component. Preferably, the connection between the two components is a non-fluid connection. The first and second fluid transport components can be described as having exterior surfaces, as having a separate channel extending therethrough forming interior surfaces, as having a flared end, and as having a tapered end. In other embodiments, the components can be described as being formed of walls that have an interior surface forming the channel and that have an exterior surface that form the outer boundary of the component. In further embodiments, the adaptor body can comprise an inlet port extending outward from the exterior surface of one of the first and second fluid transport components. Preferably, the inlet port is in fluid connection with the component from which it extends. In other embodiments, the inlet port may be described as intersecting a wall of one of the components to form an opening therein.

In some embodiments, the adaptor further can comprise one or more sealing members. For example, a sealing member may be located at the interior surface of one or both of the flared ends of the first and second fluid transport components. In some embodiments, the wall of one or both of the fluid transport components may have formed therein a groove or the like for receiving a sealing member, such as an O-ring or a gasket. Of course, any other means useful for positioning the sealing member such that it at least partially extends into the channel formed in the fluid transport component could be used. For example, a washer or other retaining member could be placed below the sealing member to prevent the sealing member from being removed through the flared end of the fluid transport component.

In preferred embodiments, the inlet port of the inventive adaptor may comprise a luer or barb connector. Such connectors are more fully described below. In specific embodiments, the luer connector may be in accordance with ISO 594-2:1998.

The alignment of the inlet port in relation to the remaining components of the adaptor body can vary. Specifically, the inlet port could have any length or geometry (i.e., substantially straight, L-shaped, curved, or the like) useful to facilitate ease of attachment of a secondary gas source to the inlet port. In specific embodiments, the inlet port is substantially perpendicular to the exterior surface of the fluid transport component. Thus, the attachment of the inlet port to the fluid transport component may be such that the exterior surfaces of the walls of the components are at about a 90° angle. Of course, such angle could vary as deemed useful. In some embodiments, the angle can be between about 10° and about 90°, between about 20° and about 90°, between about 30° and about 90°, between about 40° and about 90°, between about 45° and about 90°, between about 50° and about 90°, or between about 60° and about 90°. In specific embodiments, the length of the inlet port may be about 1 cm to about 5 cm, about 1.5 cm to about 4.5 cm, about 1.5 cm to about 4 cm, or about 1.5 cm to about 3 cm. Preferably, the alignment, shape, and length of the inlet port provide for ready access while the adaptor is inserted in-line between an endoscope control body and a water source connector. Component geometry also may be related to the fluid transport components of the adaptor body. For example, the first and second fluid transport components may be described as being substantially parallel. Moreover, they may be described as being in a side-by-side connection. As will be evident from the further disclosure herein, such alignment can be particularly useful to facilitate use with specific types of endoscope devices, and any adaptor not having such alignment or structure would be expressly excluded from being used in connection with the specific type of endoscope device. Specifically, in some embodiments, the inventive adaptor can be designed and shaped for attachment specifically to an Olympus-manufactured endoscopic device. Such specificity can arise from the specific structure and placement of elements on the Olympus-manufactured endoscope devices for delivery of fluid into the endoscope (such as from a water bottle). The adaptor of the present invention may be expressly structured for insertion in-line in an Olympus-manufactured endoscope and water bottle connector assembly.

In specific embodiments, the fluid transport components may be described in relation to the specific type of fluid to be transferred therethrough. For example, the first fluid transport component may be referred to as a liquid transport component. Thus, the channel formed therein could be referred to as a liquid channel. Similarly, the second fluid transport component may be referred to as a gas transport component. Thus, the channel formed therein could be referred to as a gas channel. Preferably, the inlet port included in the adaptor extends outward from and is in fluid connection with the gas transport component. Thus, the channel formed in the gas inlet port would be in fluid connection with the gas channel in the gas transport component.

In some embodiments, it may be useful for the various components of the adaptor body to have specific shapes or dimensions. For example, in some embodiments, the internal diameter of the gas channel at the tapered end of the channel can be greater than the internal diameter of the liquid channel at the tapered end of the channel. Similarly, in some embodiments, the external diameter of the liquid channel at the flared end of the channel can be greater than the external diameter of the gas channel at the flared end of the channel.

Sizes and dimensions of the specific components of the inventive adaptor can be specifically determined for use with specific devices. For example, endoscope control bodies manufactured by Olympus Optical Company, Ltd. are known to include two pins for fluid transfer to and from a water bottle via attachment to receptacles formed in a water bottle connector. In certain embodiments, the inventive adaptor may be formed to specifically interact with such pins and receptacles. For example, in one embodiment, the flared ends of the first and second fluid transport components from the inventive adaptor may be shaped to engage the fluid transport elements or pins extending from a portion of an endoscopic device, such as in the Olympus devices. More particularly, the flared ends may be shaped to facilitate a press-fit, sealed engagement with the fluid transport elements on the endoscopic device without secondary engaging means. This is particularly beneficial because of the ease of use of a press-fit adaptor and the ability to prepare such adaptors in a very cost-effective manner that passes on the cost savings to an end-user. Moreover, the press-fit adaptor would be useful with an endoscopic device while avoiding fluid loss since known in-line devices typically include secondary means for securing the device, such as a screw collar or the like.

Similar to the above, in other embodiments, the tapered ends of the first and second fluid transport components can be shaped to engage receptacles in a water source connector. Again, the tapered ends can be shaped to facilitate a press-fit, sealed engagement with the water source connector receptacles without secondary engaging means.

In some embodiments, the present invention may be distinguishable from the art based on the overall structure of the adaptor. For example, as described above, the adaptor body may be formed of the first fluid transport component, the second fluid transport component, and the inlet port, and these components may be combined into a single, monolithic structure. Specifically, the adaptor body may be formed as a single item that is shaped to provide the separate components. Such nature of the inventive adaptor may arise from the method of formation of the adaptor and the material used to form the adaptor. Specifically, the adaptor body may be formed of a polymeric material. As such, the adaptor body may be described as being formed of a plastic material. In some embodiments, the polymeric material used to prepared an adaptor body according to the invention may be a material that is chemical resistant, heat resistant, or both chemical resistant and heat resistant. Other components used in an adaptor according to the invention (e.g., retaining members) may likewise be formed of such polymeric materials and, preferably, may be formed of the same material as the adaptor body.

In one embodiment, the adaptor body may be described as being a single piece of polymeric material having two channels formed therein. Preferably, the two channels do not intersect and are not in fluid connection. One channel may be a liquid channel and the other channel may be a gas channel. Both channels preferably are linear and may be substantially or completely straight (although the channel walls may have a slight draft angle, such as up to about 5°, up to about 4°, up to about 3°, up to about 2°, or up to about 1°. The gas channel may be branched and may be described as being substantially T-shaped, one line extending the length of the adaptor (i.e., from the tapered end to the flared end) and the other line extending through the inlet port, for example, the second line extending substantially perpendicularly from the first line.

In an additional aspect, the adaptor includes a shroud for providing additional rigidity. The shroud may extend radially outwardly from the exterior surfaces of the first and second fluid transport components, as well as axially with respect to the first and second fluid transport components so as to at least partially surround the tapered end of the first and/or second fluid transport component. The shroud may include a wall extending circumferentially about the first and second fluid transport components so as to define an opening for at least partially receiving the tapered end of the first and/or second fluid transport component. In one embodiment, the shroud extends axially such that the tapered end of the second fluid transport component is completely surrounded by the shroud, and the tapered end of the first fluid transport component is not completely surrounded by the shroud.

In light of the foregoing description, it is clear that the inventive adaptor also may be described in terms of the method of manufacture. For example, the adaptor, particularly the adaptor body, may be described as being a molded part.

Thus, in some embodiments, the invention also can provide a method of preparing an adaptor for secondary gas provision in an endoscope. The method can comprise providing a mold shaped to form an adaptor body that is a single, integral piece of polymeric material having two channels formed therein, injecting a polymer into the mold, and allowing the polymer to harden. Preferably, after the molding process, the edges of the adaptor body are free and clear of flashing and flecking. Further, preferably, the molding process is free of any mold release agent such that the molded part is free of any mold releasing agent. Moreover, preferably, the molding process is controlled such that the finished part is free and clear of any grease or other lubrication used in a molding tool.

In another aspect, the invention can provide methods of carrying out an endoscopic procedure. In one embodiment, a method according to the invention can comprise using an assembly including an endoscopic device, a water source, a gas source, and an adaptor according to any embodiment disclosed herein.

In a specific embodiment, a method for supplying a secondary gas in an endoscopic procedure can comprise the following steps: using an endoscope device having attached thereto a water source with a connector; affixing between the water source connector and the endoscope device an adaptor according to the present invention; and supplying a secondary gas to the endoscope device via the gas inlet port on the adaptor. Specifically, the adaptor can comprise an adaptor body having: a liquid transport component in non-fluid connection with a gas transport component, the transport components each having exterior surfaces, each having a separate channel extending therethrough forming interior surfaces, and each having a flared end and a tapered end; and a gas inlet port extending outward from the exterior surface of the gas transport component and being in fluid connection with the component. Preferably, the secondary gas comprises carbon dioxide, although other gases or combinations of gases could be used.

BRIEF DESCRIPTION OF THE DRAWINGS

Figure 1:
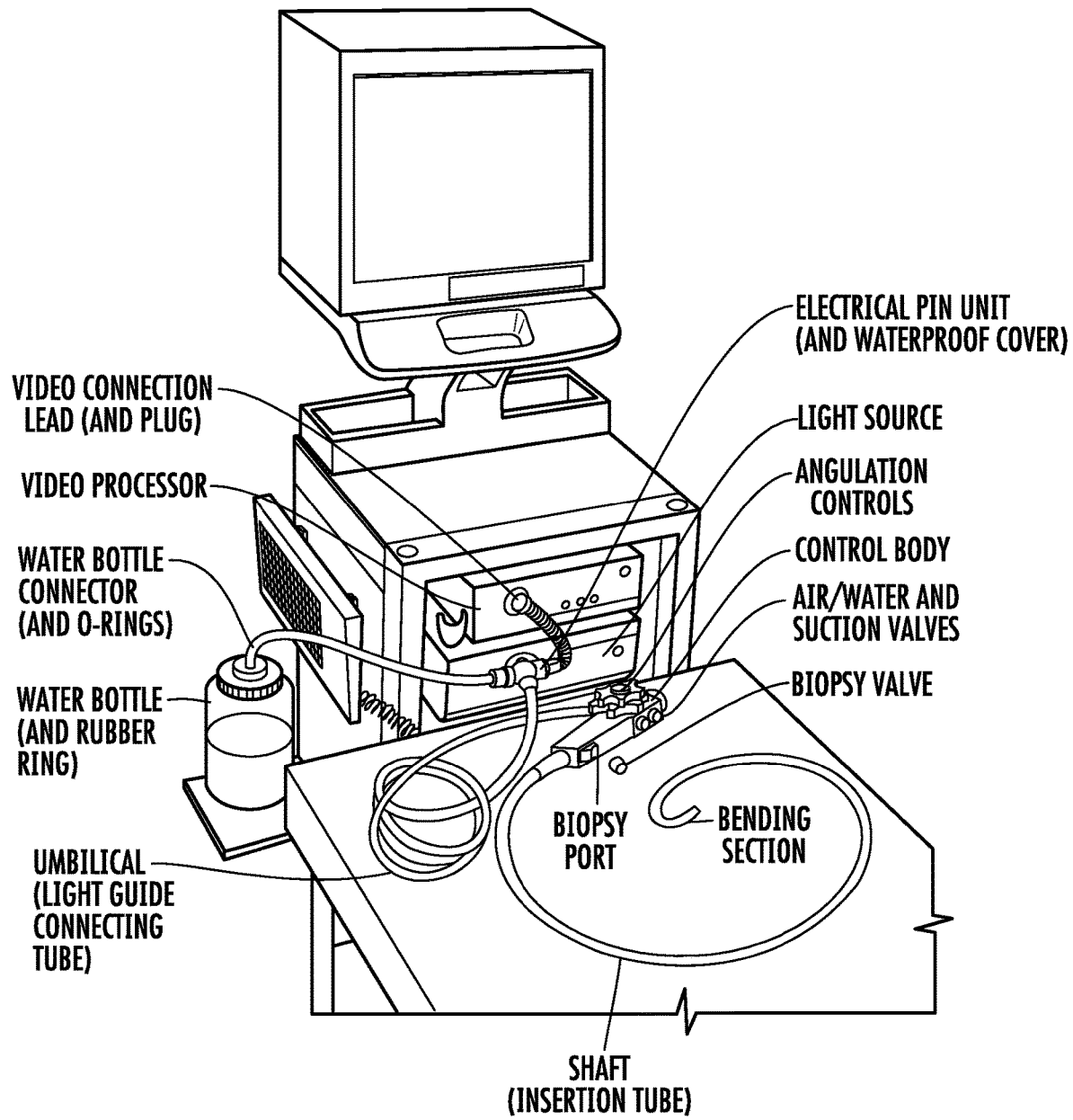
Figure 2:
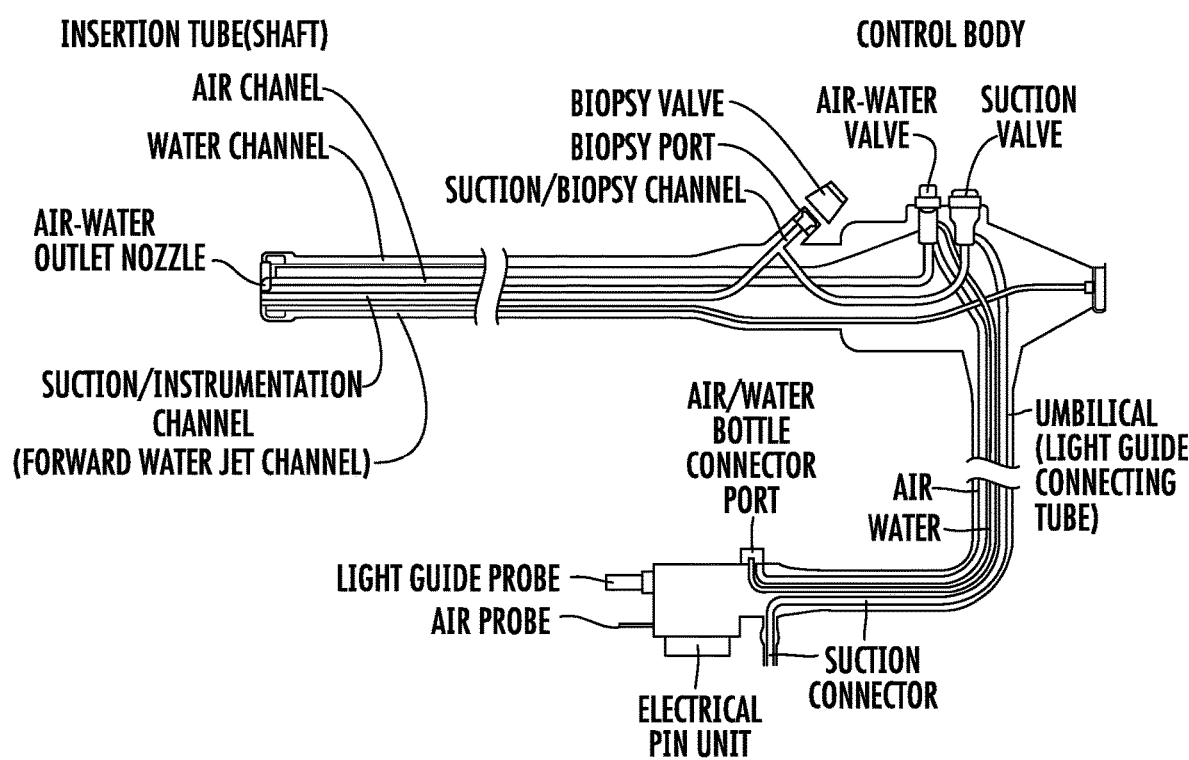
Figure 3:
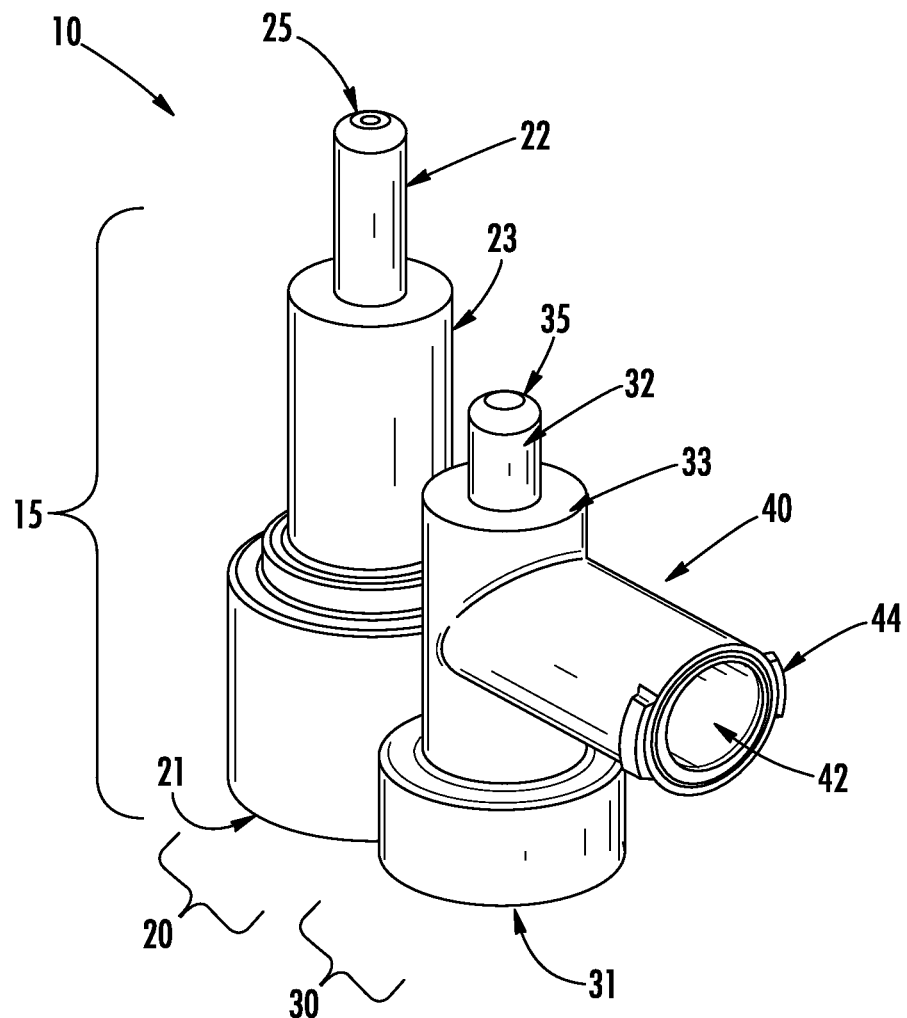
Figure 4:
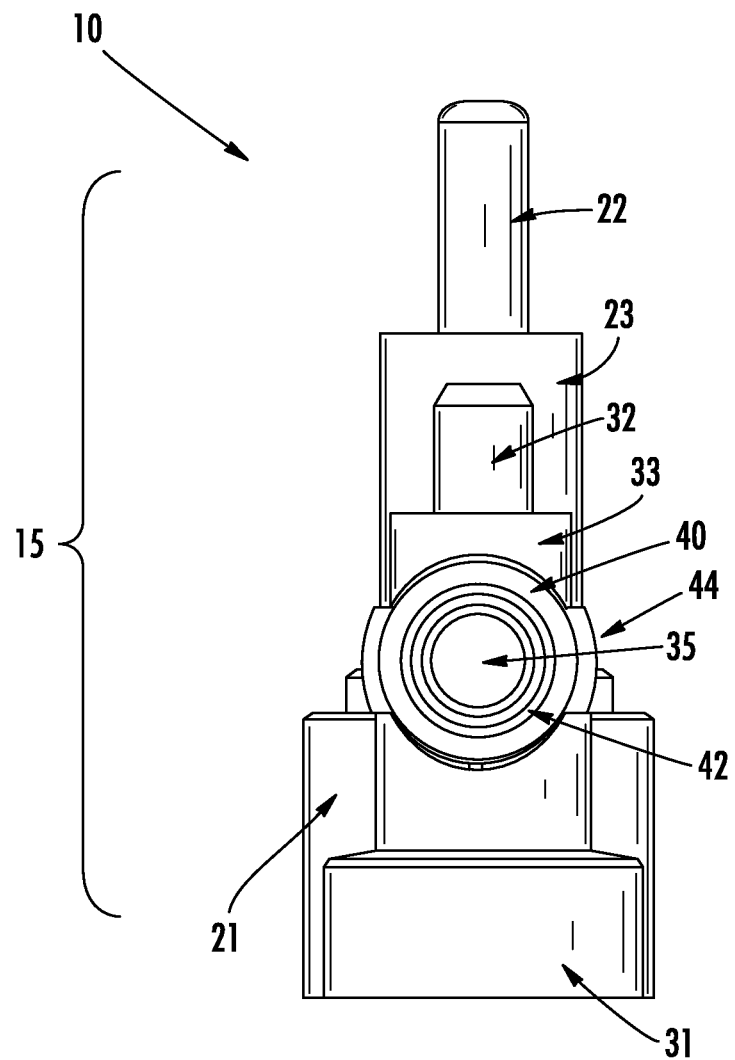
Figure 5:
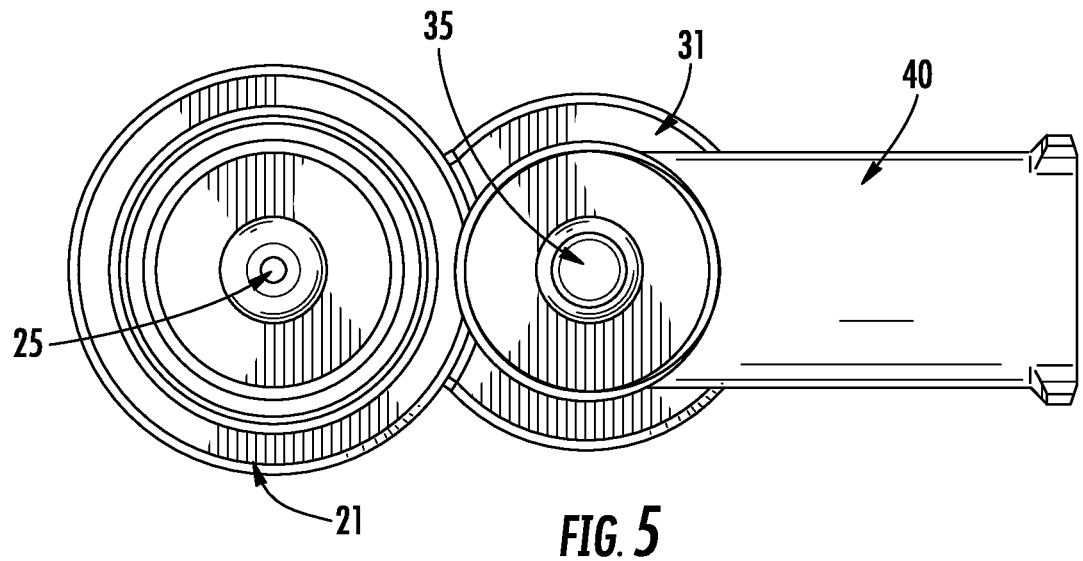
Figure 6:
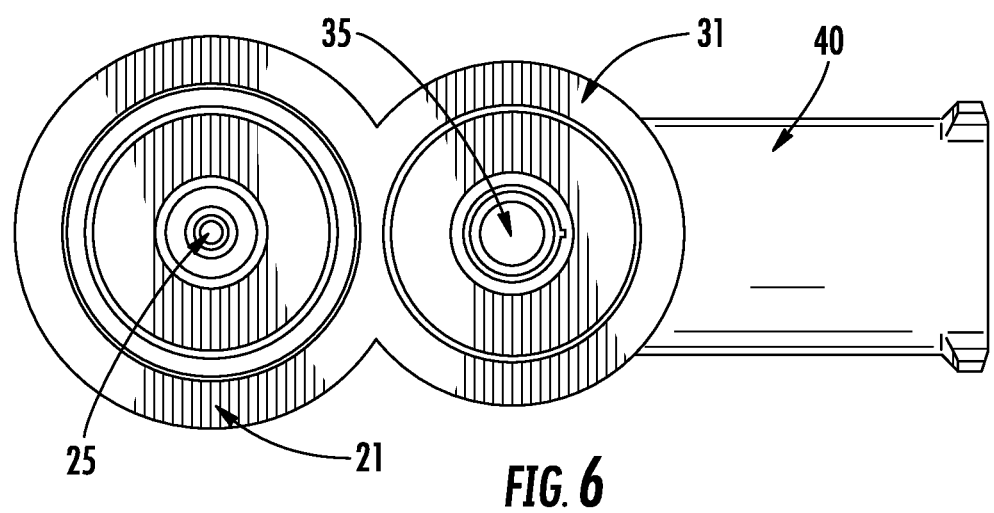
Figure 7:
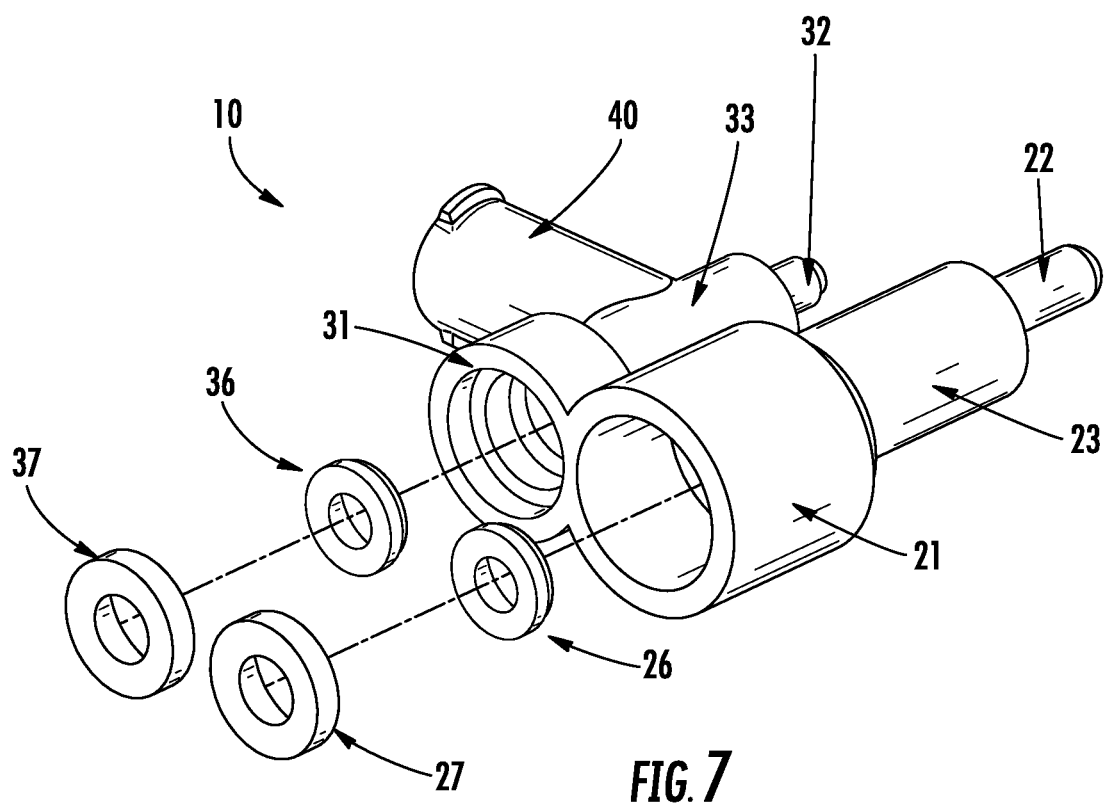
Figure 8:
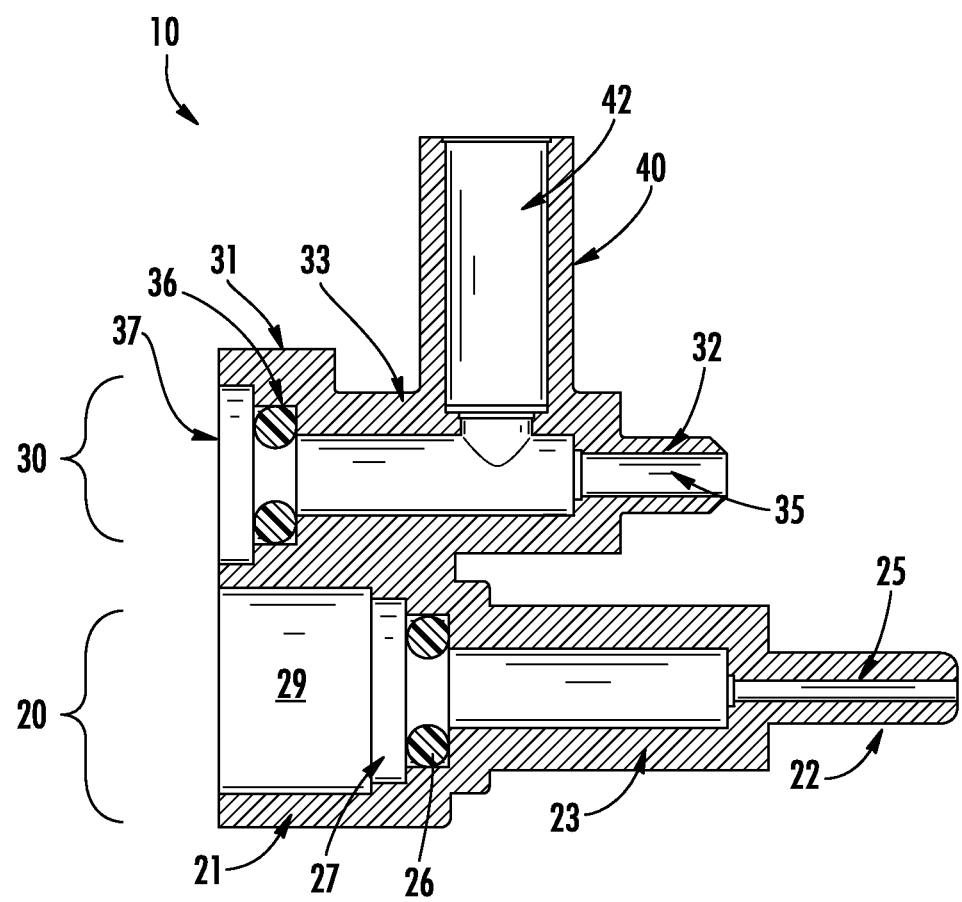
Figure 9:
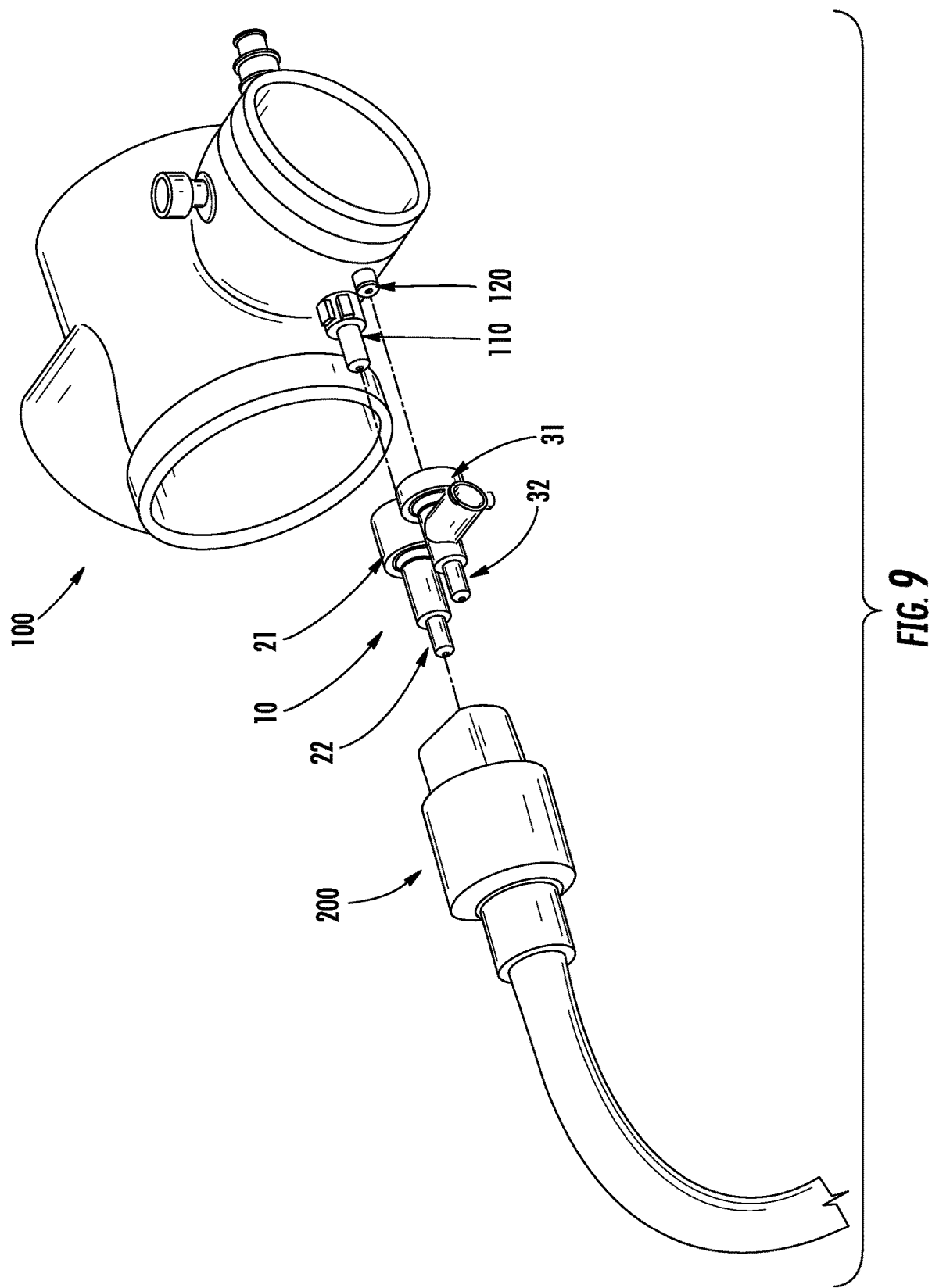
Figure 10:
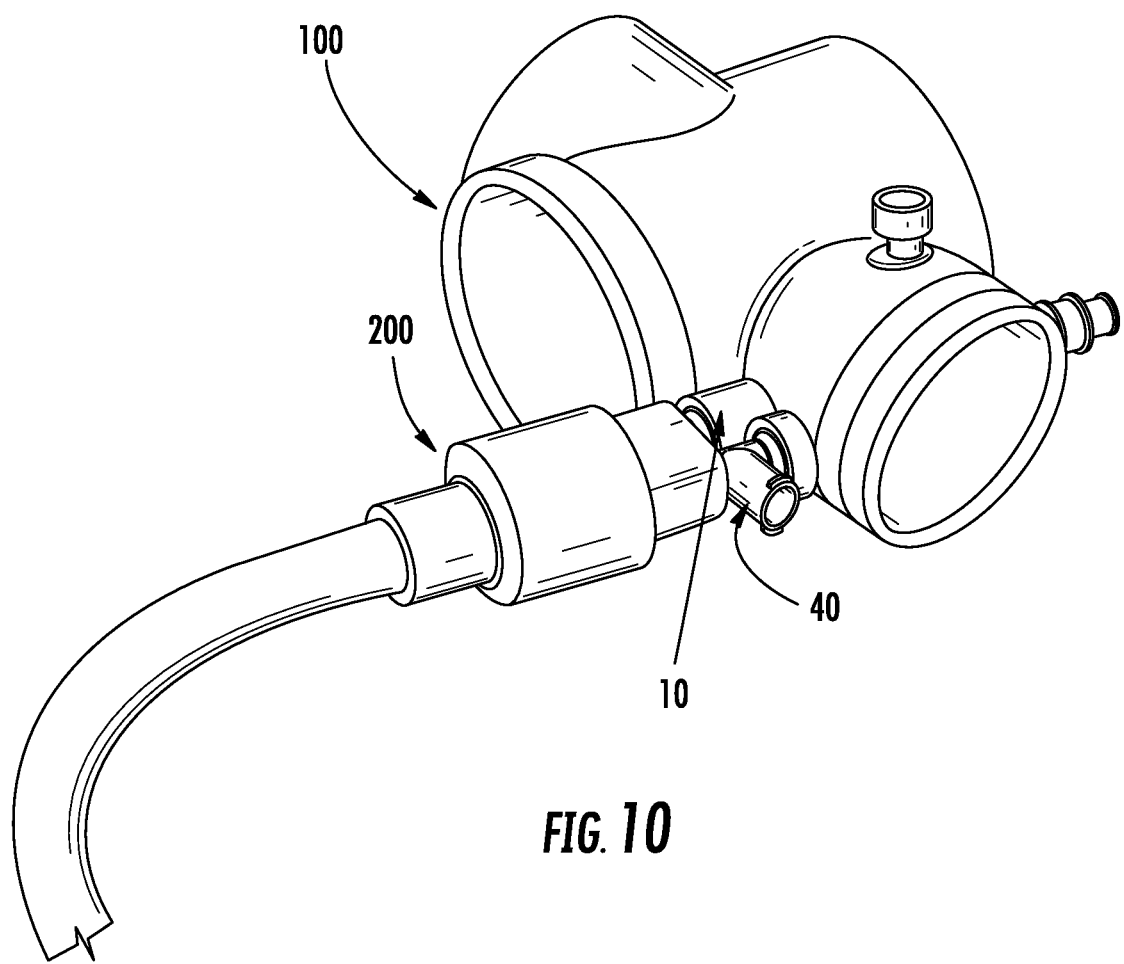
Figure 11:
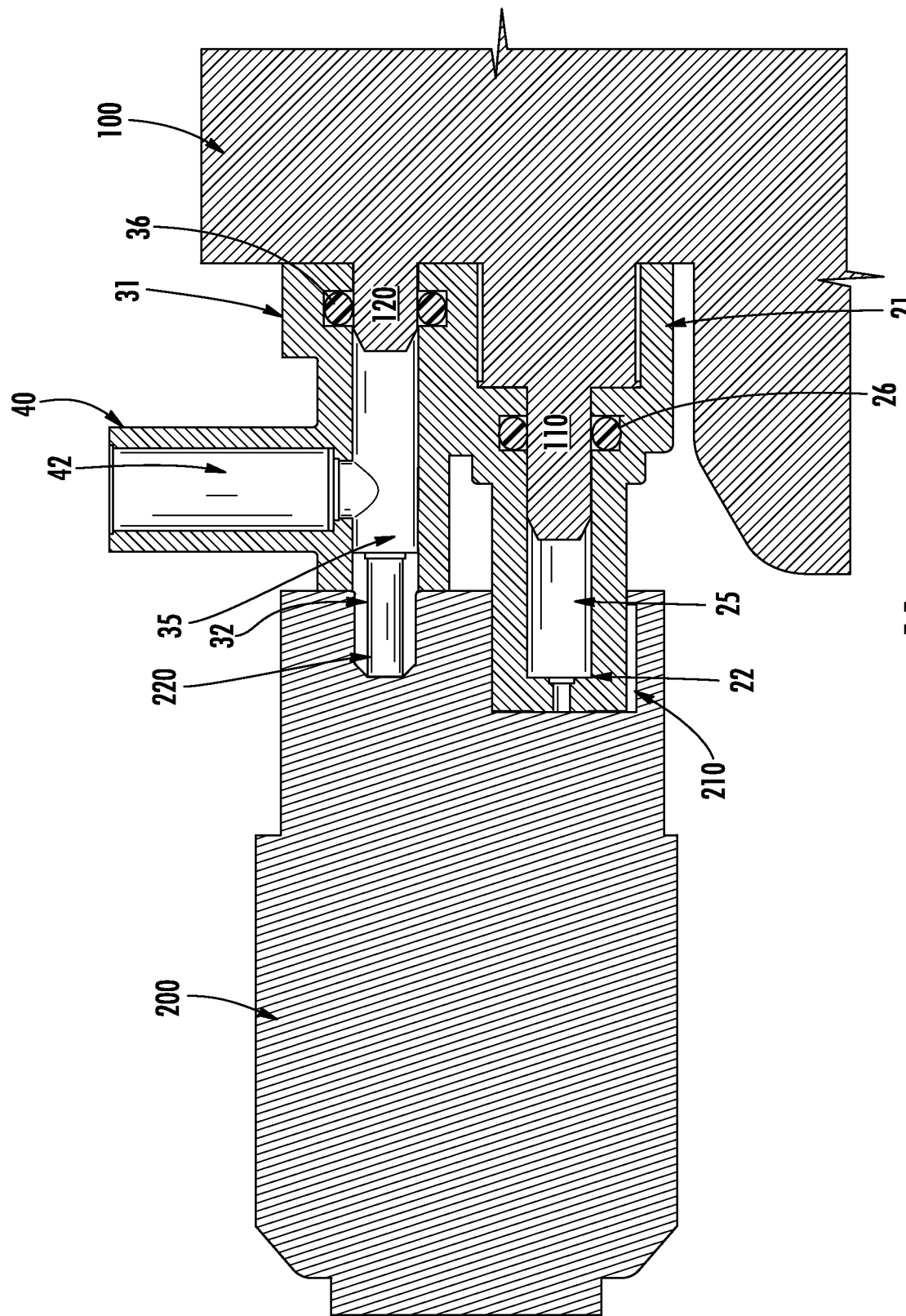
Figure 12:
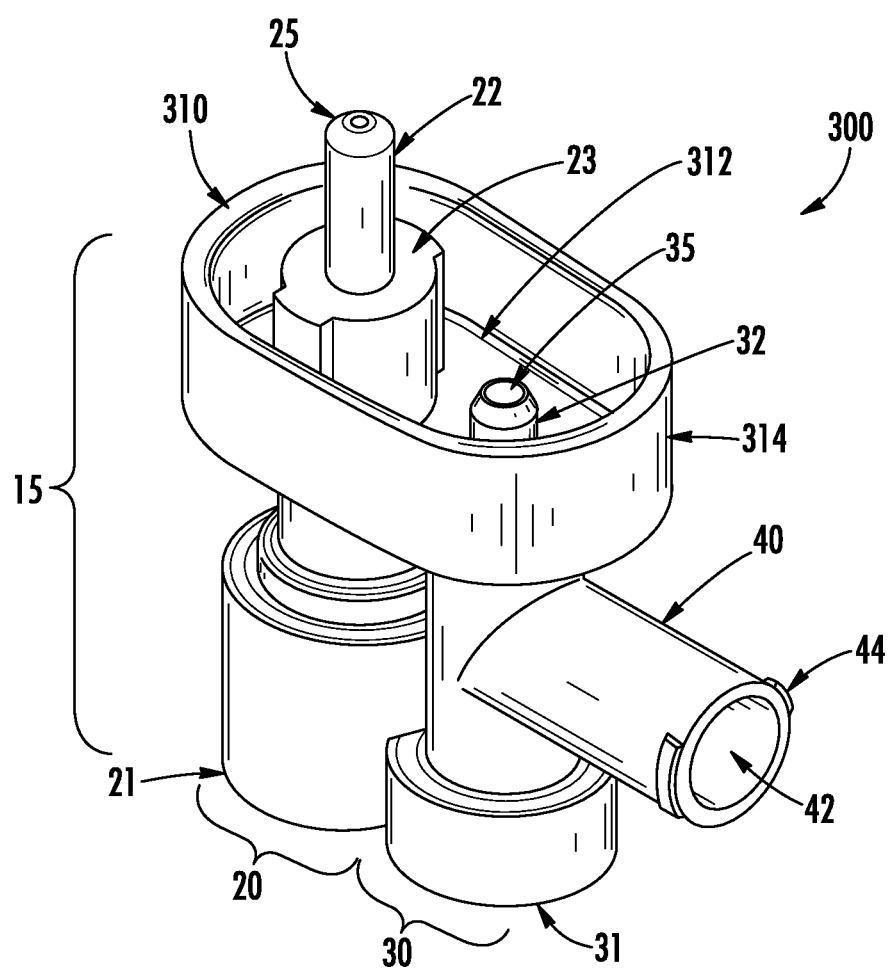
Figure 13:
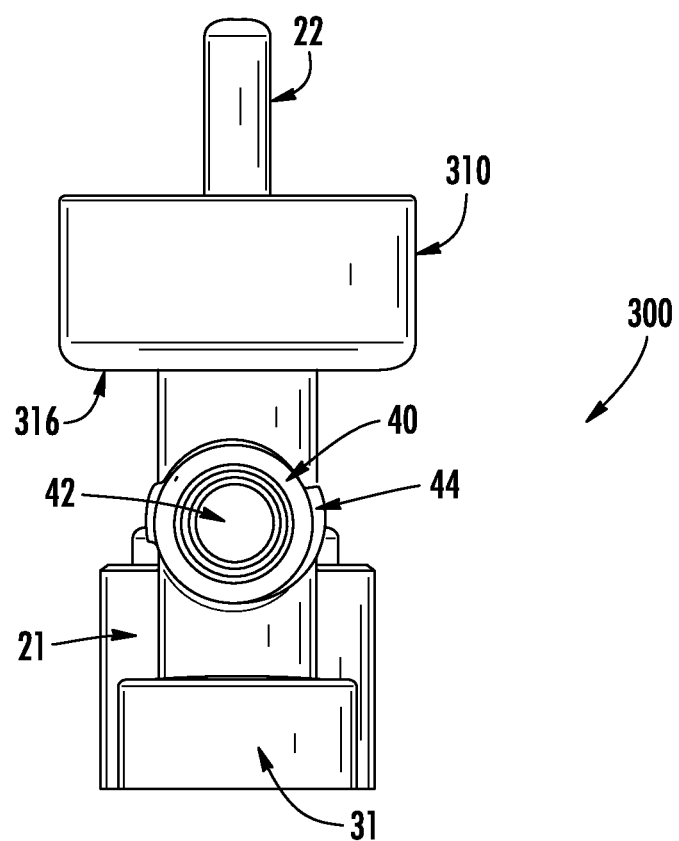
Figure 14:
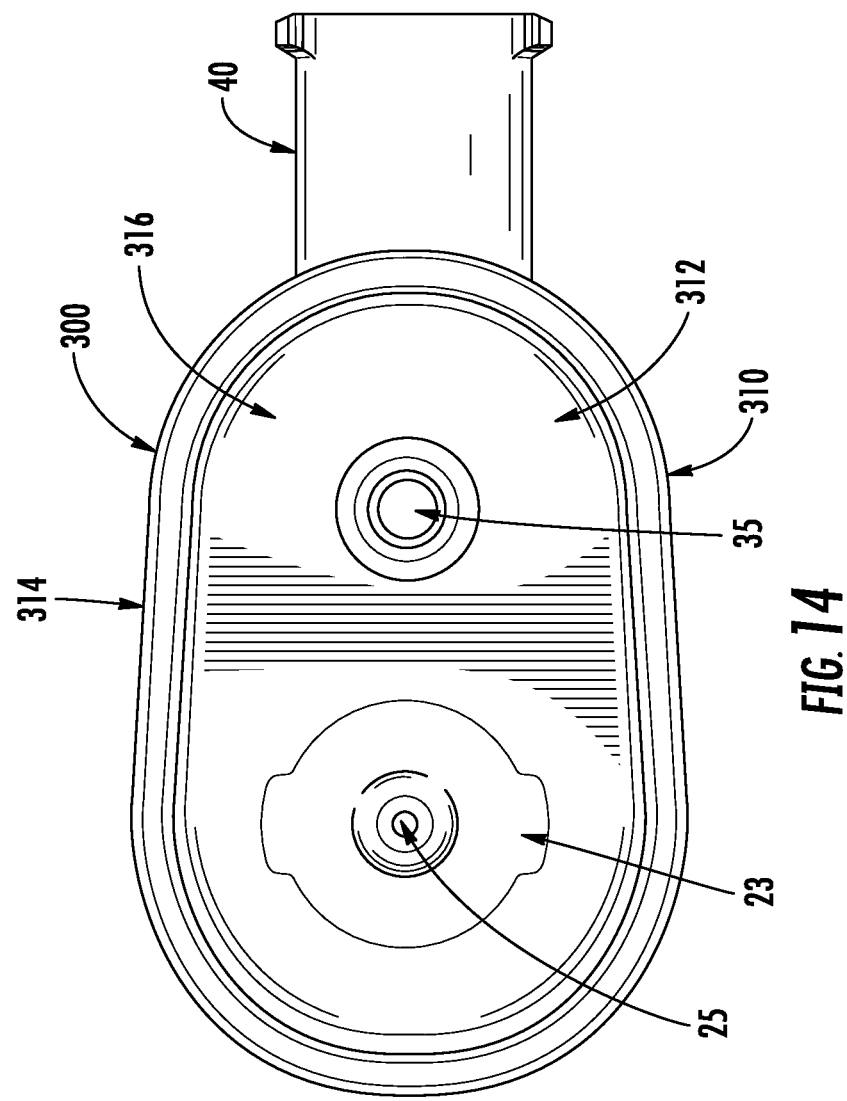
Figure 15:
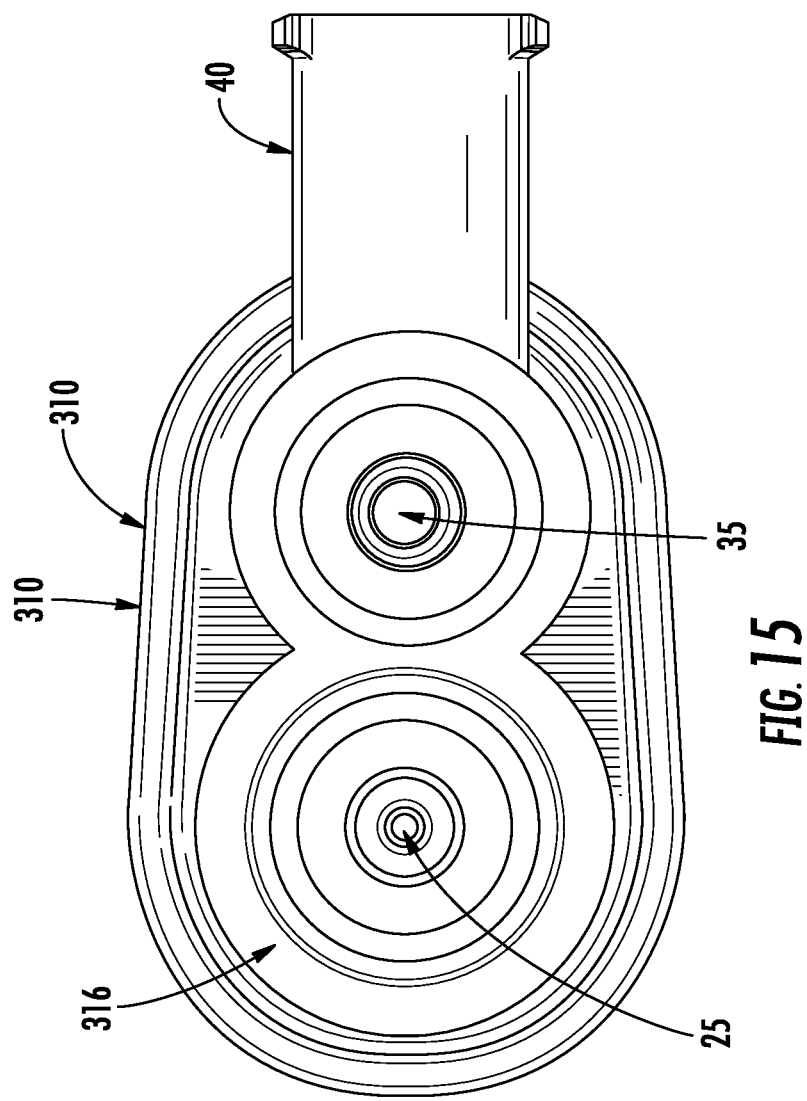
Figure 16:
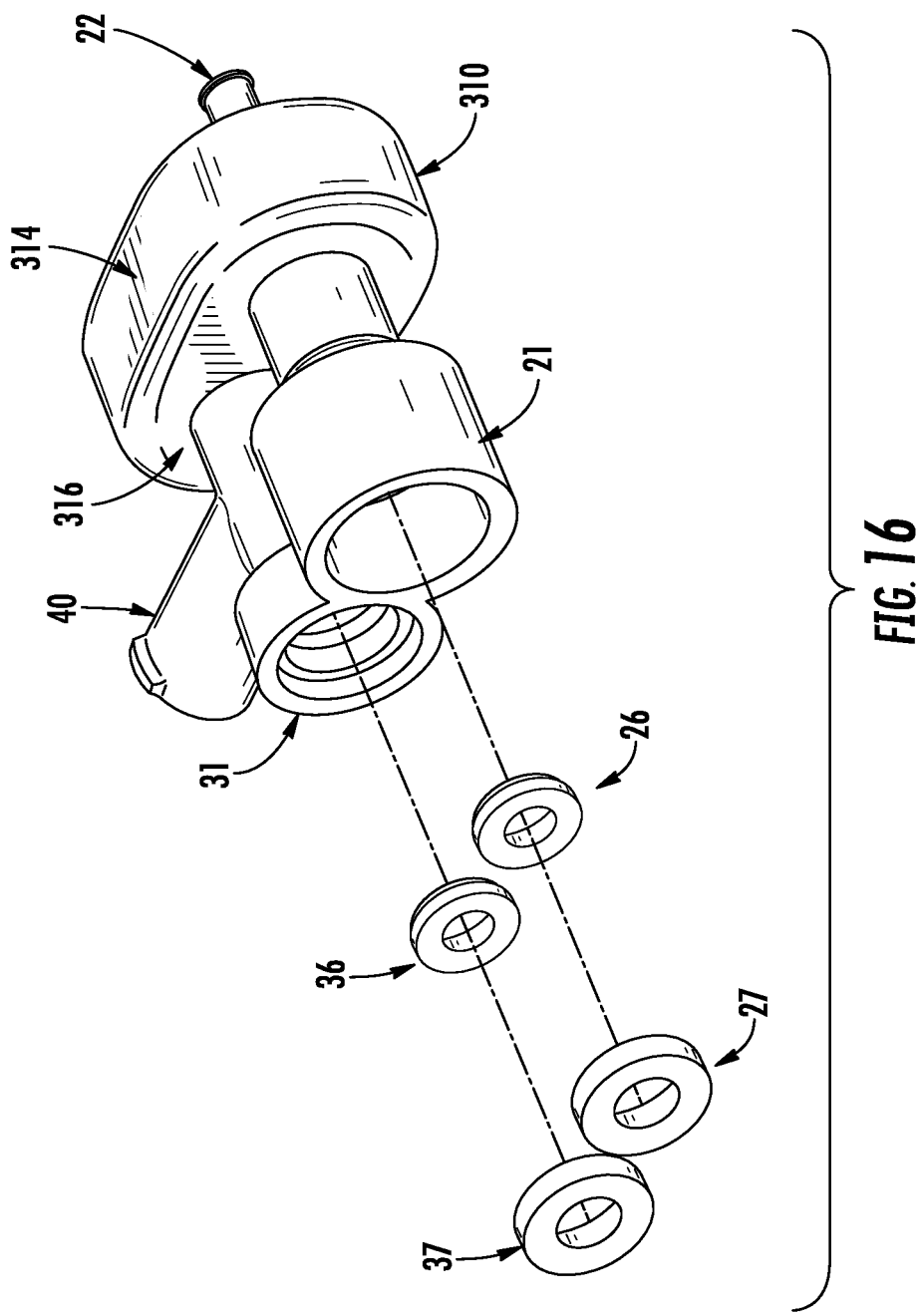
Figure 17:
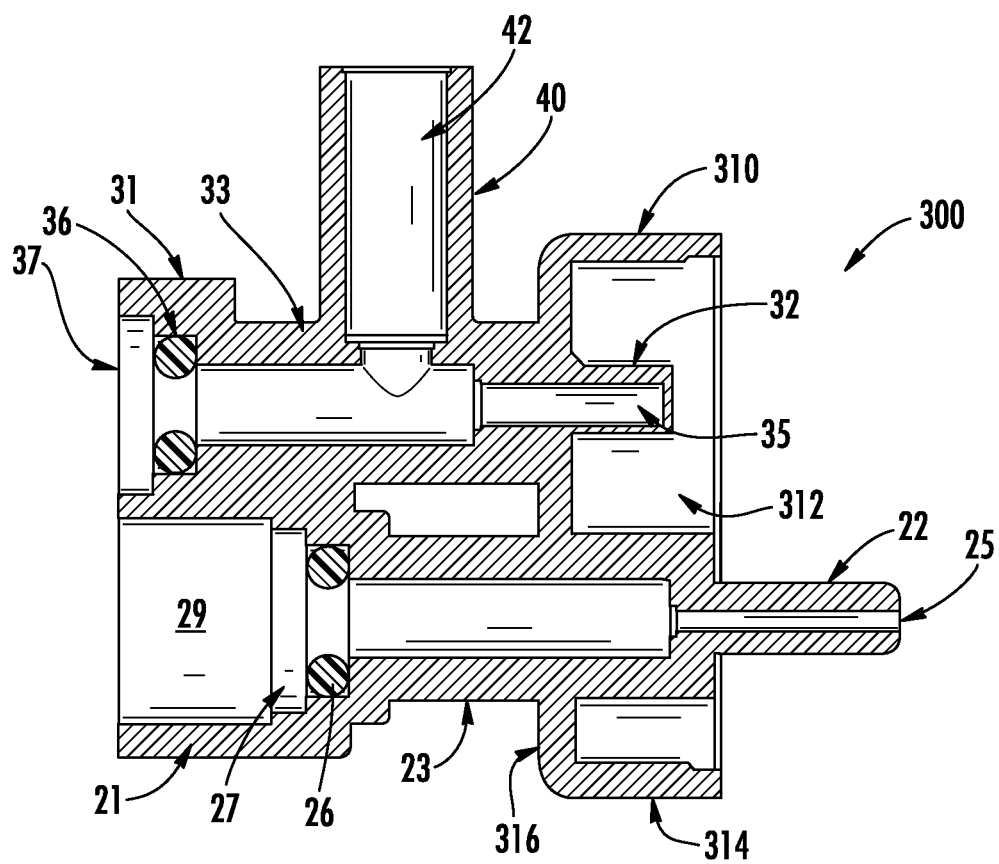
Figure 18:
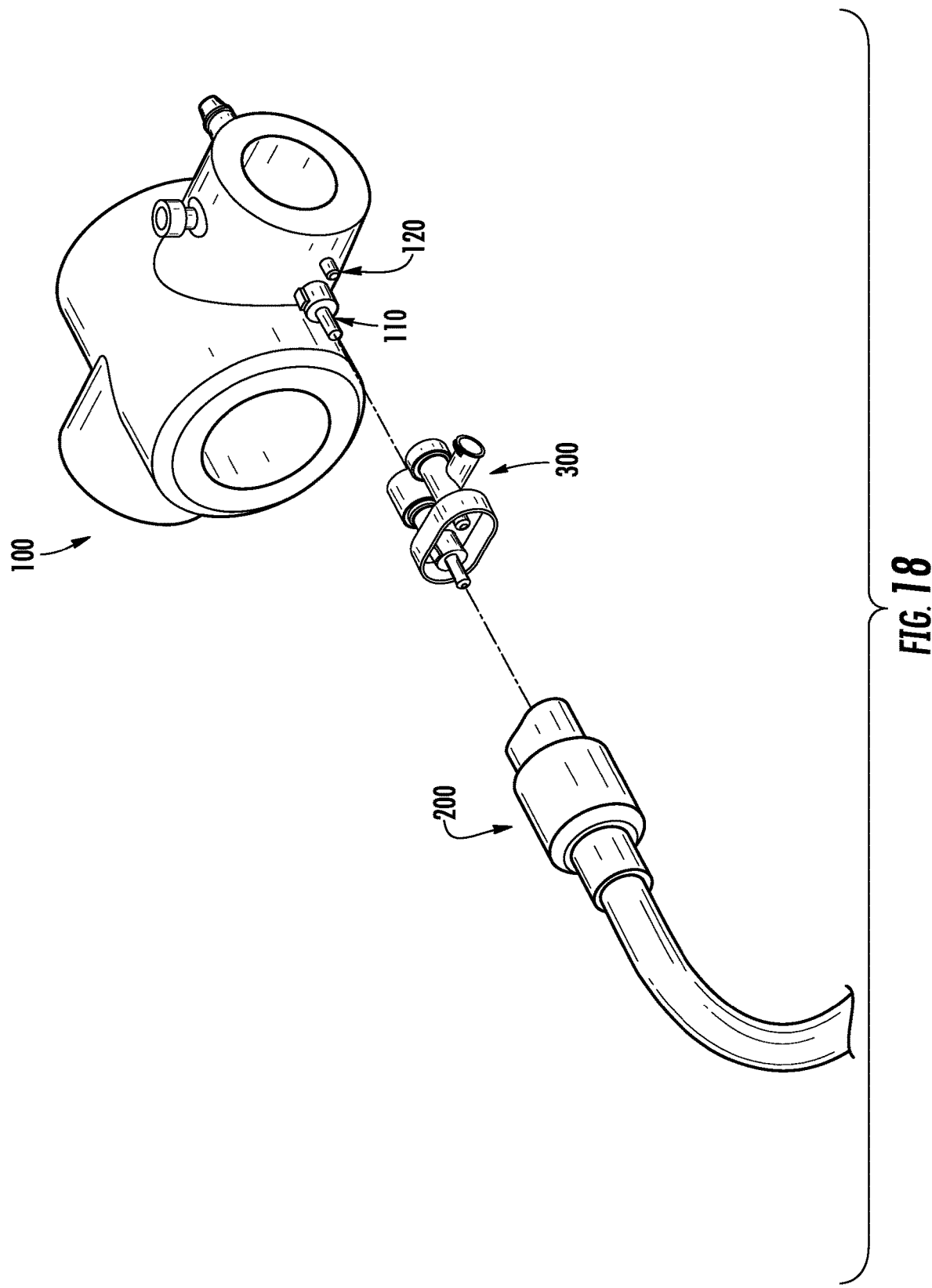
Figure 19:
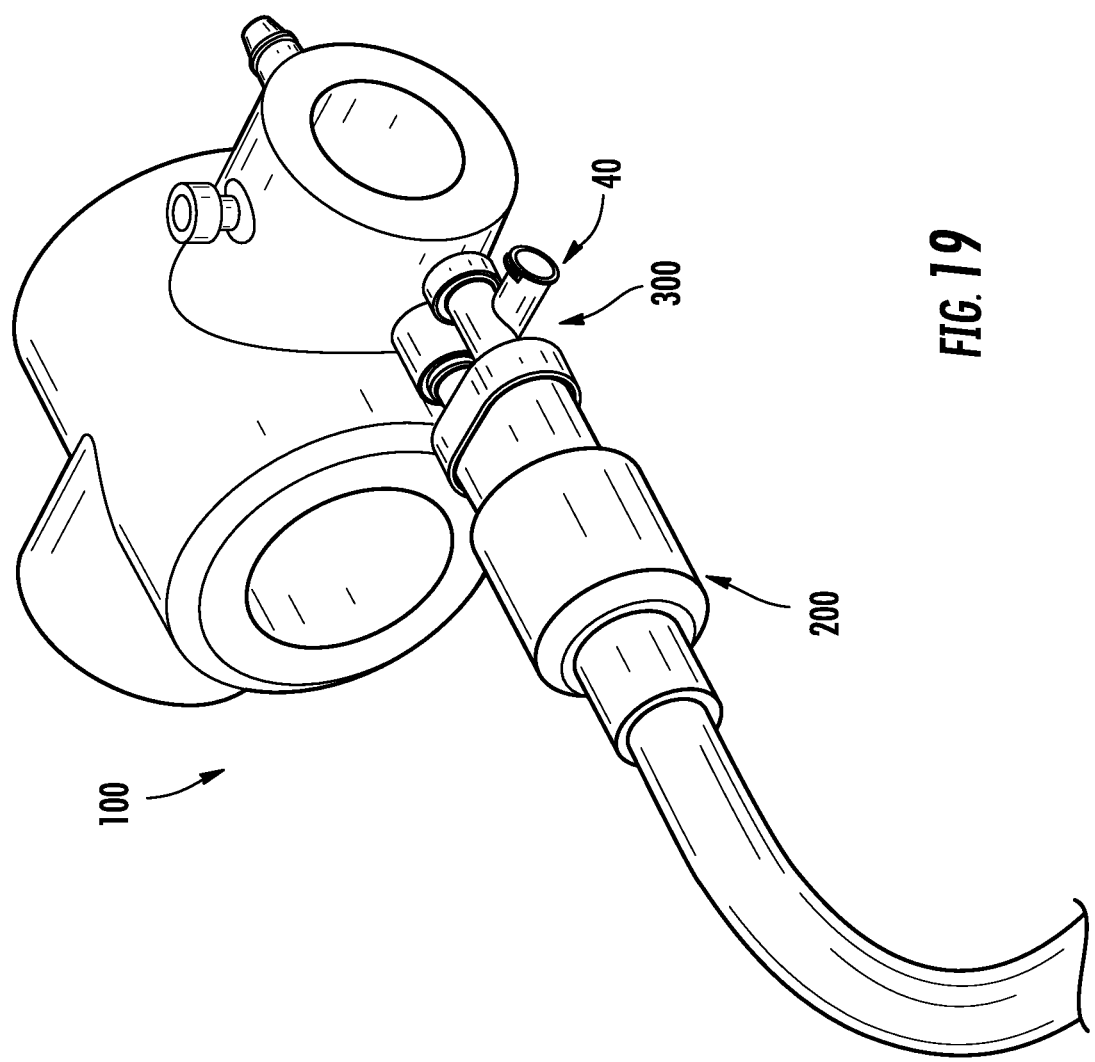
Figure 20:
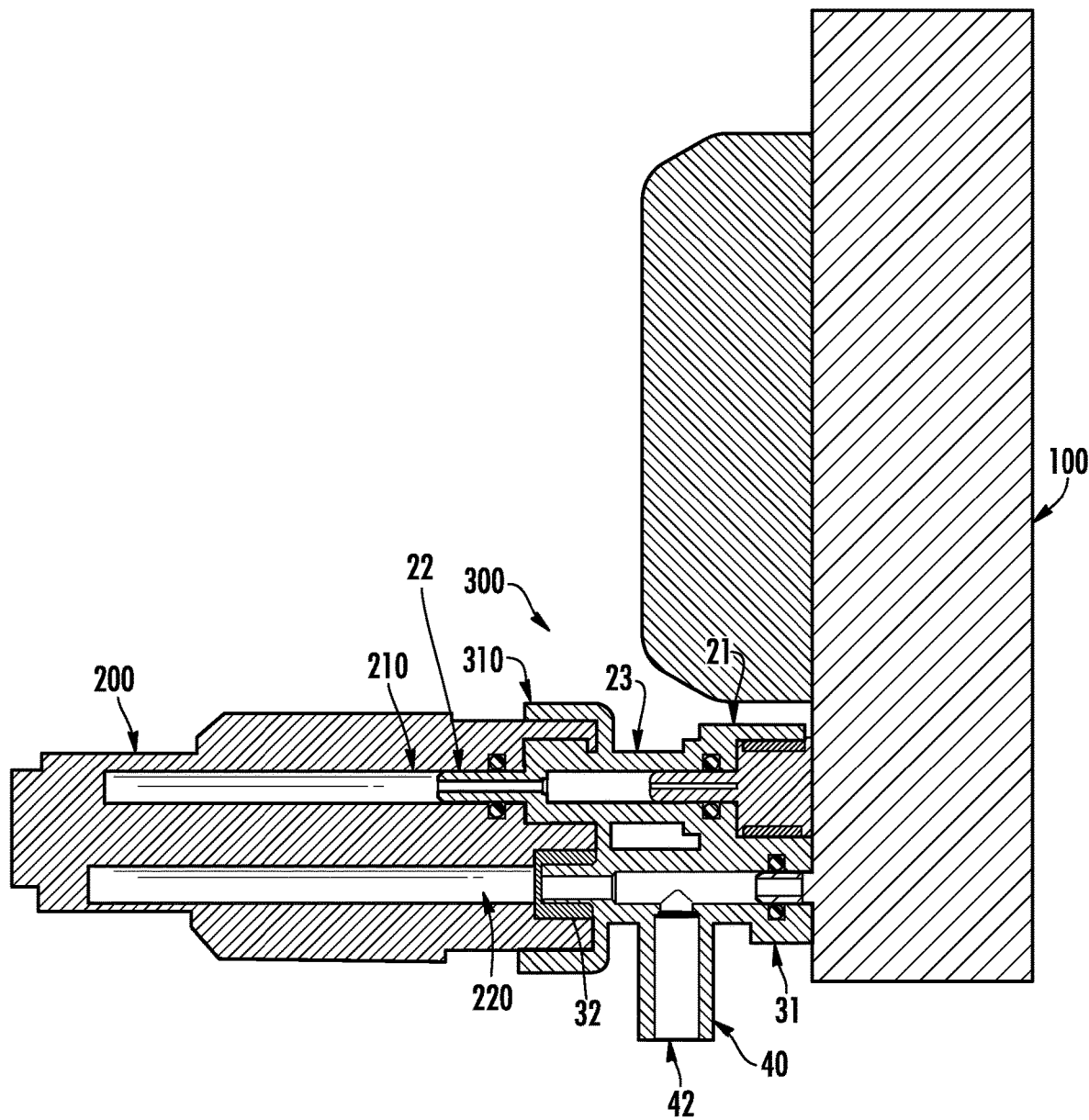

Having thus described the invention in general terms, reference will now be made to the accompanying drawings, which are not necessarily drawn to scale, and wherein:

FIG. 1 is an illustration of an unmodified endoscope system that includes no means of providing a secondary gas supply;

FIG. 2 is a detailed view of the endoscope from the system illustrated in FIG. 1;

FIG. 3 is a perspective view of an adaptor according to one embodiment of the invention;

FIG. 4 is a front view of an adaptor according to one embodiment of the invention;

FIG. 5 is a top view of an adaptor according to one embodiment of the invention;

FIG. 6 is a bottom view of an adaptor according to one embodiment of the invention;

FIG. 7 is an exploded view of an adaptor according to one embodiment of the invention;

FIG. 8 is a cross-section of an adaptor according to one embodiment of the invention;

FIG. 9 is an exploded view showing an adaptor according to one embodiment of the present invention in position for placement in-line between a water source connector and the control body of an endoscope device;

FIG. 10 illustrates an adaptor according to one embodiment of the invention placed in-line between a water source connector and the control body of an endoscope device;

FIG. 11 is a cross-section showing the press fit, in-line attachment of an adaptor according to one embodiment of the invention placed between a water source connector and the control body of an endoscope device;

FIG. 12 is a perspective view of an adaptor according to another embodiment of the invention;

FIG. 13 is a front view of an adaptor according to one embodiment of the invention;

FIG. 14 is a top view of an adaptor according to one embodiment of the invention;

FIG. 15 is a bottom view of an adaptor according to one embodiment of the invention;

FIG. 16 is an exploded view of an adaptor according to one embodiment of the invention;

FIG. 17 is a cross-section of an adaptor according to one embodiment of the invention;

FIG. 18 is an exploded view showing an adaptor according to one embodiment of the present invention in position for placement in-line between a water source connector and the control body of an endoscope device;

FIG. 19 illustrates an adaptor according to one embodiment of the invention placed in-line between a water source connector and the control body of an endoscope device; and FIG. 20 is a cross-section showing the press fit, in-line attachment of an adaptor according to one embodiment of the invention placed between a water source connector and the control body of an endoscope device.

DETAILED DESCRIPTION

The invention now will be described more fully hereinafter through reference to various embodiments. These embodiments are provided so that this disclosure will be thorough and complete, and will fully convey the scope of the invention to those skilled in the art. Indeed, the invention may be embodied in many different forms and should not be construed as limited to the embodiments set forth herein; rather, these embodiments are provided so that this disclosure will satisfy applicable legal requirements. As used in the specification, and in the appended claims, the singular forms "a", "an", "the", include plural referents unless the context clearly dictates otherwise.

The present invention provides an adaptor that allows for the use of any secondary gas during an endoscopic procedure. Endoscopic assemblies typically include a water source, such as a water bottle. These often include caps that have a dual-lumen tube that supplies air through one lumen to charge the water bottle. This charge gas may be considered a primary gas. Any gas provided during an endoscopic procedure in addition to or in lieu of this charge gas may be considered to be a secondary gas according to the present invention.

Introduction of a gas into a body cavity is common practice in gastrointestinal endoscopic procedures. Previously, when it has been desired to introduce a gas during an endoscopic procedure, standard room air was simply introduced (such as from the light source). More recently it has been found that the use of carbon dioxide ($CO_2$) insufflation can improve post-procedure patient comfort since $CO_2$ is more easily absorbed by the body. For example, use of $CO_2$ may be particularly useful for long endoscopic exams, such as endoscopic retrograde cholangiopancreatogram (ERCP), enteroscopy, and colonoscopy, and gas may be used in other endoscopic procedures as well, such as endoscopic ultrasound (EUS) and esophagogastroduodenoscopy (EGD). Provision of a secondary gas source has proven challenging, however. For example, the addition of $CO_2$ in an endoscopic procedure has previously required the use of cumbersome external regulators, flow meters, and specialized valves. The advent of specialized equipment for the provision of a secondary gas in an endoscopic procedure, such as the $CO_2$EFFICIENT™ Endoscopic Insufflator (available from Bracco Diagnostics, Inc., Princeton, N.J.), has simplified secondary gas supply. Still, though, the lack of standardization in endoscopic devices made by different manufacturers continues to complicate the provision of a secondary gas in association with a variety of endoscopic devices. For example, Pentax has available a gas adaptor that is designed exclusively for its endoscopic devices. The Pentax adaptor, though, is relatively expensive, is designed for multiple uses, and can be difficult to use (for example requiring attachment via a screw collar). This design raises the issues of cost and patient safety associated with the cleaning of reusable parts. Olympus and Fujinon have each addressed the provision of a secondary gas when using their respective endoscopic devices by providing water bottles with bottle caps that include some means for attaching a gas source. Again, the cost of these parts can be prohibitive and sterilization between uses is still required. In contrast, the present invention has made possible the addition of a secondary gas in a manner that is easy to use, medically safe, and economical.

The ability to use any secondary gas of choice according to the invention can be achieved through provision of an adaptor for use "in-line" with an endoscopic device. As discussed previously, endoscopic devices typically include a main body to which a number of different cord, tubes, or lines are attached. This provides for introduction of light, fluids, and instruments into the body of a patient. As used herein, the term "in-line" is understood to mean that the adaptor is designed to function with an endoscopic device by being positioned between two or more components of the device. Thus, "in-line" can mean that the adaptor is positioned between two or more of a main body, a cord, a tube, a line, a connector, or the like. A skilled person readily would be able to envision the different parts of an endoscopic device where an adaptor according to the invention would be positioned to provide the function described herein. In specific embodiments, an adaptor according to the invention is designed for positioning in-line between the main body of an endoscopic device and the cord, tube, or line leading to a water source. Specifically, the adaptor may connect at one end to the main body of the endoscopic device and at another end to a water bottle connector.

In one aspect, the present invention provides an adaptor for an endoscopic device. The adaptor particularly is designed to be positioned in-line with existing components of an endoscopic device. Such design is evident by the disclosure provided hereinafter.

In certain embodiments, the adaptor generally can comprise an adaptor body. The adaptor body may encompass the bulk of the overall adaptor. In other words, the adaptor body may be substantially a single, integral component. Of course, further components may be included, as described below, but the adaptor body may be characterized by its single, integral nature, such as the express lack of any movable parts needed to secure the adaptor to the remaining components of an endoscopic device. In specific embodiments, the adaptor body may be described as being formed of a first fluid transport component, a second fluid transport component, and an inlet port that together are a single, monolithic structure. The term monolithic is understood as meaning that the overall adaptor body is a unitary structure having a seamless construction that cannot be separated into its individual components without the use of destructive means, such as cutting the components apart.

Although the adaptor body preferably exhibits a single, integral structure, the structure of the adaptor can be described in relation to the function and shape of the various components or areas of the adaptor. For example, in some embodiments, the adaptor body may be described as having a first fluid transport component and a second fluid transport component. As used herein, the term "fluid" is intended to encompass any material that may be described in relation to flow, such as a gas or a liquid, including solutions or other physical forms of a liquid or a gas that may include some concentration of a solid material in a dissolved, suspended, or otherwise mixed state that does not prevent flow of the liquid or gas. Although the adaptor is discussed and illustrated in terms of a first and a second fluid transport component, the adaptor is not limited to only two such components. Rather, the adaptor could include further fluid transport components for use with devices where three or more fluids may be transported through a common carrier (e.g., a liquid and two or more gases, a gas and two or more liquids, or two or more gases and two or more liquids).

As the adaptor body is a single component, it is preferable that the first and second fluid transport components be attached or connected. In specific embodiments, though, the first and second fluid transport components can be in a "non-fluid connection," which is understood to mean that walls of the separate fluid transport components may be connected or attached one to another, but the fluid transport means of each component are maintained separate from one another such that any fluid transported through the first component cannot become intermixed with the fluid transported through the second component. In other embodiments, if desirable, the fluid transport components could be in a fluid connection.

The first and second fluid transport components may be described as having exterior surfaces and interior surfaces. The exterior surfaces can encompass the external structure of the adaptor body (e.g., the shape and dimensions) and, as discussed in more detail below, the external structure can facilitate interconnection of the adaptor with other devices. The exterior and interior surfaces may be described in relation to the walls of the adaptor (i.e., the walls of the adaptor body generally or the walls of the specific components, such as walls forming the channels, walls delineating the fluid transfer components, and walls forming the inlet port).

The interior surfaces of the first and second fluid transport components can encompass a channel that extends through the fluid transport components and facilitates movement of a fluid from one end of the adaptor to another end of the adaptor. Preferably the channel extending through the first fluid transport component is separate from the channel extending through the second fluid transport component. As discussed in more detail below, the interior surface of the fluid transport components also can encompass areas that facilitate interconnection of the adaptor with other devices.

The fluid transport components also may be described in relation to the shape and dimensions of the ends of the adaptor. For example, the fluid transport components each may have a flared end and a tapered end. Likewise, the adaptor generally may be described as having a flared end and a tapered end. As seen in relation to the Figures, the flared and tapered ends can be designed specifically to facilitate interconnection of the adaptor with certain elements of an endoscopic device or assembly. In some embodiments, the interior of the flared end may be considered part of the channel extending through the fluid transport component. In other embodiments, the interior of the flared end may be considered to be separate from the channel. For example, the interior of the flared end may be considered a receiving element for receiving a connector or other fluid transport element extending from another device.

In addition to the fluid transport components, the adaptor body also can comprise an inlet port. The inlet port can be any element extending outward from the exterior surface of a fluid transport component and being in fluid connection with the component. The inlet port also can be described as being a substantially tubular shaped element and/or as forming a channel that intersects one of the previously described channels formed in the adaptor body, particularly formed in one of the above-described fluid transport components. The inlet port particularly can be the element that allows for introduction of a secondary gas, as more particularly described below.

The structure and function of the inventive adaptor are further seen in relation to the various Figures. For example, FIG. 3 illustrates an adaptor 10 according to the invention. The adaptor body 15 comprises a first fluid transport component 20 and a second fluid transport component 30. It is understood that the terms "first" and "second" are meant for ease of understanding and are not intended to limit the invention. For example, in FIG. 3, the left side of the adaptor is described as the first fluid transport component. In other embodiments, the right side of the adaptor could be described as the first fluid transport component.

In FIG. 3, the first fluid transport component 20 comprises a flared end 21 and a tapered end 22 separated by a first central body 23. The first fluid transport component 20 also comprises a channel 25 extending therethrough (only the opening at the tapered end 22 being visible). Also in FIG. 3, the second fluid transport component 30 comprises a flared end 31 and a tapered end 32 separated by a second central body 33. The second fluid transport component 30 also comprises a channel 35 extending therethrough (only the opening at the tapered end 32 being visible).

The body 15 of the inventive adaptor 10 also comprises an inlet port 40. The inlet port particularly can be a gas inlet port. As such, the fluid transport component to which the gas inlet port 40 is connected can be referred to as the gas transport component. As illustrated in FIG. 3, the second fluid transport component 30 could be described as the gas transport component 30 Likewise, the channel 35 could be described as the gas channel 35. In this embodiment, the first fluid transport component 20 thus could be described as the liquid transport component 20. Likewise, the channel 25 could be described as the liquid channel 25.

The gas inlet port 40 may take on a variety of structures and can have any structure or take on any form suitable to carry out the intended function, which is to provide a port for inputting a secondary gas into the device. In practice, a secondary gas often may be provided via some type of tubing that may or may not include a specialized connection unit (e.g., a screw-on connection or a plug-in connection). For example, the gas inlet port 40 could include a barb, thread, or snap fitting connection. Thus, the gas inlet port 40 may be designed to accommodate such a specialized connection. In one embodiment, the tubing may be coupled between the gas inlet port 40 and an insufflator unit inputting the secondary gas. Regardless of the type of connection that is to be accommodated, the gas inlet port 40 can comprise a central passage 42 extending through the wall of the gas transport component 30 and opening on the interior surface of the gas transport component 30. Such central passage 42 can be solely for passage of the secondary gas or also can form an entry port for insertion of a gas connection. For example, if the gas is to be provided via a device having a specialized plug-in connector, the passage 42 can be formed to accommodate the plug. Thus, the passage 42 can be described as being an annular passage with walls that may have formed therein specialized components (e.g., grooves or threads) for receiving a plug. The components particularly may allow for removable attachment of a plug device for delivery of gas.

In specific embodiments, the gas inlet port 40 may substantially extend outward from the exterior surface of the gas transport component 30. Such a structure particularly is useful to accommodate attachment of a gas line having a screw-on component or a gas line that attaches by simply being pressed over and onto the extending portion of the port 40 (e.g., a standard, flexible hose or tube).

In one embodiment, the gas inlet port 40 may comprise a luer connector or any similar structure. Luer connection systems typically are associated with the interconnection of syringes, catheters, hubbed needles, IV tubes, and the like. A luer connection system consists of round male and female interlocking tubes that may be slightly tapered to hold together better with even just a simple pressure/twist fit. As illustrated in FIG. 3, the luer connector is a female component. In use, a male luer connector may simply slip inside the shown female component and form a secure connection. The illustrated embodiment provides for an even more secure fit through inclusion of an additional outer rim 44 (which functions as a single thread). As shown, the rim 44 is formed of two separate "wings." In use, the male luer connector can include an additional outer rim of threading to form a "locked" connection.

An adaptor according to certain embodiments of the invention also is shown in FIG. 4 as a front view (i.e., looking directly at the gas inlet port 40). As seen in this embodiment, the gas inlet port 40 can be formed to be substantially perpendicular to the exterior surface of the fluid transport components 20 and 30. As also seen in this embodiment, the first fluid transport component 20 and the second fluid transport component 30 can be in substantially parallel alignment and can be in a side-by-side connection. Such alignment is beneficial to facilitate attachment of the adaptor 10 to the components of the endoscopic device. The fluid connection between the gas inlet port 40 and the gas transport component 30 is also seen in FIG. 4. Specifically, the figure shows the central passage 42 of the gas inlet port 40 opening into the gas channel 35 in the gas transport component 30. Thus, the central passage 42 can be viewed as being separate from the gas channel 35 or can be viewed as being a branch of the gas channel 35.

As seen in the embodiment of FIG. 4, the external surfaces of the fluid transport components of the adaptor 10 may have different relative dimensions. For example, the flared portion 21 of the first fluid transport component 20 may have an outside diameter that is greater than the outside diameter of the flared portion 31 of the second fluid transport component 30. In other embodiments, the flared portion 21 of the first fluid transport component 20 may have an outside diameter that is less than the outside diameter of the flared portion 31 of the second fluid transport component 30, of the diameters may be substantially equal. Likewise, the overall length of the first fluid transport component 20 may be greater than the overall length of the second fluid transport component 30. In other embodiments, the overall length of the first fluid transport component 20 may be less than the overall length of the second fluid transport component 30, or the overall lengths may be substantially equal. Similarly, the overall length of the flared portion 21 of the first fluid transport component 20 can be greater than the overall length of the flared portion 31 of the second fluid transport component 30. In other embodiments, the overall length of the flared portion 21 of the first fluid transport component 20 can be less than the overall length of the flared portion 31 of the second fluid transport component 30, or the overall lengths may be substantially equal. Further, the length of the central body 23 of the first fluid transport component 20 can be greater than, less than, or substantially equal to the length of the central body 33 of the second fluid transport component 30. Moreover, the length of the tapered end 22 of the first fluid transport component 20 can be greater than the length of the tapered end 32 of the second fluid transport component 30. In other embodiments, the length of the tapered end 22 of the first fluid transport component 20 can be less than the length of the tapered end 32 of the second fluid transport component 30, or the lengths can be substantially equal.

Top and bottom views of an adaptor 10 according to the invention are shown in FIG. 5 and FIG. 6, respectively. As can particularly be seen in FIG. 5, the internal diameter of the gas channel 35 at the tapered end 32 thereof can be greater than the internal diameter of the liquid channel 25 at the tapered end 22 thereof.

The adaptor of the invention may include further components in addition to those already described. Such further components may be separate from the monolithic structure of the adaptor body. Such further components may be formed separately from the monolithic structure of the adaptor body but may be combined with the adaptor body in such a manner so as to effectively become an integral part of the overall structure.

In certain embodiments, such as illustrated in FIG. 7, the adaptor 10 further may comprise one or more sealing members. As illustrated, an O-ring 26 is included in the flared end 21 of the first fluid transport component 20 and a second O-ring 36 is included in the flared end 31 of the second fluid transport component 30. Of course, other types of sealing members, such as gaskets or the like, are encompassed by the invention. As further described below, the sealing members are useful for forming a fluid-tight connection between the adaptor and the devices to which it is attached.

The adaptor 10 also can comprise retaining members for retaining the sealing members within the flared ends of the fluid transport components. As illustrated in FIG. 7, the adaptor 10 includes a first washer 27 that is included in the flared end 21 of the first fluid transport component 20 external to the O-ring 26 and a second washer 37 that is included in the flared end 31 of the second fluid transport component 30 external to the second O-ring 36. Although washers are illustrated, the invention should not be so limited. Rather, any means useful to retain the sealing members in position could be used. For example, the flared ends could include a lip or other similar member formed on the internal surface of the flared ends such that that sealing member could be accessed. Likewise, the sealing members could be positioned in grooves formed in the walls of the adaptor body, said grooves functioning to retain the sealing members in place.

When a washer or similar component is used, the means for positioning the washer within the flared ends of the fluid transport components can vary. For example, the washer could be glued into position or could be welded. The formation of the retaining members is limited only in the ability to form the member during formation of the adaptor body.

The overall structure of an adaptor 10 according to one embodiment of the invention particularly is illustrated in the cross-section provided in FIG. 8. As seen therein, the adaptor body can be described as being a single, unitary structure with a number of channels formed therein. It can be seen that the first fluid transport component 20 is integrally formed with the second fluid transport component 30. Thus, the two components are connected, but the connection is non-fluid in that there is no pathway or channel where a fluid from one component could be intermingled with a fluid from the other component.

As is particularly evident in FIG. 8, the interior of the adaptor body can be designed specifically to receive further components, as described above. For example, in the region of the flared ends 21 and 31 of the two components 20 and 30, the interior of the adaptor body can have a stepped structure. In this embodiment, an open area 29 is provided in the flared end 21 of the first fluid transport component 20. This area particularly can be provided to facilitate attachment to a fluid transport element extending from a portion of an endoscopic device, as further described below. In the embodiment illustrated, no such open area is provided in the flared end 31 of the second fluid transport component 30 because the fluid transport element on an endoscopic device to which the second fluid transport component is to be attached does not include a widened area that requires such an opening. Of course, in other embodiments, a similar open area could be provided in the second fluid transport component. Likewise, the open area could be absent in the first fluid transport component or both components.

The cross-section of FIG. 8 also further illustrates the presence of walls that interconnect to form a series of channels. Specifically, the walls of the adaptor body form a liquid channel 25, a gas channel 35, and a secondary gas inlet channel 42. In other embodiments, the secondary gas inlet channel simply can be a branch of the gas channel 35, and the walls of the adaptor can be viewed as forming two channels, one linear channel and one branched channel.

The adaptor of the invention can be made of a variety of different materials, which may affect how the adaptor is formed. In certain embodiments, the adaptor may be a machined part. As such, the adaptor particularly may comprise a plurality of individual parts that are machined separately and then combined to form the final adaptor assembly. Such combination can be by any means recognized as useful in the art, such as gluing, welding or the like or using further attachment components, such as rivets, or the like.

In preferred embodiments, the inventive adaptor may be a molded part. This particularly is advantageous for providing the adaptor body as a single, monolithic structure. For example, the adaptor body can be formed as a single, monolithic structure formed of the fluid transport components and the inlet port. This provides for a seamless construction. In embodiments where the adaptor is reusable, this simplifies cleaning and ensures no contaminants remain in seams, etc. existing between multiple parts that may be combined to form the adaptor. When the molding method permits of such construction, the retaining members or like components (e.g., a retaining lip or ledge) could be molded into the inner surface of the flared ends of the adaptor. In other embodiments, the adaptor body could be formed as a single, monolithic structure, and the washers could be provided separately. The final adaptor can be prepared by inserting sealing members, inserting the retaining members, and attaching the retaining members to the flared ends. Thus, the final adaptor can be formed to have no moving parts.

The adaptor of the invention is also beneficial in that it can be provided as a single-use adaptor or may be provided as a reusable adaptor. In some embodiments, the inventive adaptor can be both single-use and reusable in that the end-user will have the option to dispose of the adaptor after a single use or sterilize the adaptor and reuse it. This is achievable in particular because of the ability to form the adaptor from a variety of materials using a variety of methods. Thus, the adaptor can be sufficiently economical to justify making only a single use to avoid the need to sterilize. At the same time, the adaptor can be sufficiently sturdy to withstand multiple sterilization procedures.

The adaptor body and the retaining members can be formed from a variety of different materials. In some embodiments, the adaptor comprises a metal material. Preferably, the metal is non-corrosive (e.g., stainless steel or aluminum). In other embodiments, the adaptor comprises a polymeric material, which preferably is chemical resistant, heat resistant, or both chemical resistant and heat resistant. The use of medical grade plastic materials is particularly desirable. In one specific embodiment, the polymeric material is a polysulfone (e.g., polyphenylsulfone) or a similar material. Non-limiting examples of further polymeric materials that may be used to form one or more component of the inventive adaptor include polyethylene (e.g., UHME-PE), polypropylene, polymethylmethacrylate (PMMA), acetal copolymers, polythermide, polycarbonate, and polyetheretherketone (PEEK). The sealing members can be formed of any material recognized as useful in forming such elements, such as natural or synthetic rubbers.

In one embodiment, the adaptor of the invention can comprise three plastic components and two O-rings. The plastic components can be the adaptor body, which can include a liquid channel and a gas channel, each channel extending through the adaptor body and opening to the exterior at opposing ends of the adaptor body. The adaptor body also can include a gas inlet that intersects the gas channel and preferably is substantially perpendicular to the liquid channel and the gas channel. Thus, the gas channel can open to the exterior at three points. The remaining plastic components can include two washers. The O-rings and the washers can be located in one end of the adaptor body. Preferably, the adaptor body comprises two flared portions at one end of the adaptor body, and the O-rings and the washers can be located in the flared portions. The flared portions can correspond to the two, separate channels of the adaptor body. The washers may be welded into their position to permanently prevent removal of the O-rings absent destruction of the adaptor.

The adaptor of the invention is particularly useful in light of the specific design thereof that enables the adaptor to be inserted in-line with a known endoscopic device. This is particularly illustrated in FIG. 9, FIG. 10, and FIG. 11.

More particularly, the adaptor of the invention can be formed for specific use with an endoscopic device from a particular manufacturer. As pointed out previously, typical endoscopic devices include a control body that connects to a variety of components; however, the connection means vary based upon the manufacturer.

Accordingly, in one embodiment, an adaptor according to the present invention can be specifically designed and shaped for attachment to an Olympus-manufactured endoscopic device. More particularly, the adaptor can be designed and shaped for insertion in-line between a water source connector and a control body of an Olympus OEM endoscope (i.e., an original equipment manufacturer endoscope manufactured by Olympus Optical Company, Ltd.).

The ability of the adaptor to be used in-line with an existing endoscopic device is shown in FIG. 9, where the inventive adaptor 10 is positioned to be attached at one end to an endoscope control body 100 and at the other end to a water source connector 200. The control body 100 includes two fluid transport elements or pins 110 and 120 extending from a portion thereof. In typical use, the fluid transport pins 110 and 120 engage receptacles 210 and 220 in the water source connector 200. The flared ends 21 and 31 of the adaptor 10 can be designed and shaped to engage the fluid transport pins 110 and 120. Specifically, at least a portion of the fluid transport pins 110 and 120 can engage an open area in one or both of the flared ends, can engage one or both of the channels 25 and 35 formed in the fluid transport components 20 and 30, or can engage both an open area in one or both of the flared ends and one or both of the channels 25 and 35. As the fluid transport pins 110 and 120 of the endoscope control body 100 are shaped to engage receptacles in the water source connector 200, the inventive adaptor 10 can be described as including receptacles that are substantially identical in shape and dimension to the receptacles formed in the water source connector. Specifically, any open area formed in the flared ends of the adaptor and/or the channels formed in the adaptor may be designed and shaped to be substantially identical in shape and dimension to the receptacles formed in the water source connector.

Similarly, the tapered ends 22 and 32 of the adaptor 10 can be designed and shaped to engage the receptacles in the water source connector 200. Depending upon the shape of the receptacles in the water source connector 200, the adaptor 10 can be formed such that at least a portion of one or both of the first and second central bodies 23 and 33 can engage the receptacles in the water source connector 200. As the receptacles of the water source connector 200 are shaped to receive the fluid transport pins 110 and 120 of the endoscope control body 100, the inventive adaptor 10 can be described as including pins that are substantially identical in shape and dimension to the pins formed on the endoscope control body for attachment to the water source connector. Specifically, the tapered ends of the adaptor and/or the central bodies of the adaptor may be designed and shaped to be substantially identical in shape and dimension to the pins formed on the endoscope control body.

The inventive adaptor particularly is advantageous in that it can be used simply as a press-fit device. Specifically, the adaptor can be designed to allow for being press-fit into engagement with the remaining components, as described above. For example, the flared ends of the adaptor can be shaped to facilitate a press-fit, sealed engagement with the fluid transport pins on the endoscopic device. Preferably, this is achieved without the use of any secondary engaging means (e.g., in the express absence of a screw collar or the like). Similarly, the tapered ends of the adaptor can be shaped to facilitate a press-fit, sealed engagement with the water source connector receptacles without the requirement of any secondary engaging means.

The inventive adaptor 10 is shown in FIG. 10 fully engaging the endoscope control body 100 and the water source connector 200. As seen in FIG. 10, the flared ends of the adaptor 10 are engaging the fluid transport pins from the endoscope control body 100, and the tapered ends of the adaptor 10 are engaging the receptacles in the water source connector 200. Moreover, the gas inlet 40 on the adaptor 10 is positioned in this engagement for ready attachment to a secondary gas source, such as a $CO_2$EFFICIENT Endoscopic Insufflator. The engagement of the inventive adaptor with the endoscope control body and the water source connector is more readily evident in the cross-section provided in FIG. 11.

FIGS. 12-20 illustrate an adaptor 300 according to another embodiment of the present invention. The adaptor 300 is similar to the embodiments of the adapter 10 described above, with the exception of a few modifications. As explained in additional detail below, the modifications to the adapter 300 may provide additional rigidity and facilitate a more secure press-fit with the water source connector 200. In particular, the adapter 300 includes a shroud 310 that extends radially outwardly from and around the first central body 23 and the tapered end 32. Thus, the central body 23 and the tapered end 32 are at least partially positioned within an opening 312 defined by a wall 314 of the shroud 310 and extend axially from a closed end 316 and through the opening 312. As shown in FIGS. 12 and 17, the wall 314 of the shroud 310 may extend axially and substantially parallel to the central axes of the first and second fluid transport components 20, 30 so as to extend circumferentially thereabout. The wall 314 may extend axially from the closed end 316 and have a height such that the central body 23 and the tapered end 32 are entirely surrounded by the shroud 300 and positioned within the opening 312, while the tapered end 22 extends axially beyond the height of the wall. However, it is understood that the wall 314 may extend at any desired height with respect to the fluid transport components 20, 30 in order to at least partially surround the fluid transport components and facilitate engagement with the water source connector 200. In addition, the shroud 300 may have a generally oval cross section, although the shroud may be a variety of shapes in order to facilitate engagement with a water source connector 200. FIGS. 14 and 15 illustrate that the shroud 300 may have a larger cross-sectional area than the tapered ends 22, 23 and the flared ends 21, 31. Moreover, the shroud 300 can be dimensioned to have different tolerances for facilitating a fluid-tight connection with the water source connector 200. The shroud 300 could also be formed of different materials, such as a stiffer material to enhance rigidity or a softer/pliable material for facilitating a fluid-tight seal.

FIG. 12 also demonstrates that the central body 23 may have alternative shapes and configurations in order to enhance structural stability and engagement with the water source connector 200. For example, the central body 23 may include a key-shaped end extending through the opening 312 of the shroud 300 that is configured to engage corresponding keyways in the water source adapter. Thus, the central body 23 may have different shapes along its length (e.g., key shaped within the opening 312 and cylindrical between the flared end 21 and the wall 316) in order to facilitate engagement with the water source connector 200.

As discussed above, the adapters may be formed of a variety of materials. In one embodiment, the adapter 300 includes components formed from different materials. For example, the tapered end 22 may be formed of a metallic material, while the remaining portions of the adapter 300 may be integrally formed of a polymeric material. Thus, the tapered end 22 may be formed of a more durable and stiff material than the remaining portions of the adapter 300 in order to more securely engage the water source connector 200. In one embodiment, the tapered end 22 may be a metallic material, while the first central body 23 may be a polymeric material molded around the tapered end to securely attach the components together via a suitable molding or other technique. It is understood that other components could be formed of metallic and/or polymeric materials. For example, the tapered end 32 could also or alternatively be formed of a metallic material.

In other aspects, the present invention also provides various methods that make use of the inventive adaptor. For example, the invention can be directed to methods of performing an endoscopic procedure. In one embodiment, the method can comprise using an assembly that includes an endoscopic device, a water source, a gas source, and an adaptor according to any of the embodiments described herein. In other words, the inventive adaptor could be combined at the point of use with an OEM endoscope, particularly an endoscope having fluid transport pins that engage receptacles in a water source connector, such as an endoscope manufactured by Olympus.

As previously noted, the present invention is particularly beneficial in that it allows for the easy and efficient delivery of a secondary gas to an endoscope. Thus, in other aspects, the present invention also can be directed to methods for supplying a secondary gas in an endoscopic procedure. In certain embodiments, the method can comprise using an endoscope device having attached thereto a water source with a connector. Particularly, the endoscope device can have fluid transport pins that engage receptacles in the water source connector. The method further can comprise using an adaptor according to any embodiment of the present invention. In particular, the method can comprise affixing between the water source connector and the endoscope device an adaptor according to the present invention and supplying a secondary gas to the endoscope device via the gas inlet port on the adaptor. Although any gas suitable for use in medical or veterinary procedures could be supplied, in particular embodiments, the secondary gas can comprise carbon dioxide.

Many modifications and other embodiments of the inventions set forth herein will come to mind to one skilled in the art to which these inventions pertain having the benefit of the teachings presented in the foregoing descriptions. Therefore, it is to be understood that the inventions are not to be limited to the specific embodiments disclosed and that modifications and other embodiments are intended to be included within the scope of the appended claims. Although specific terms are employed herein, they are used in a generic and descriptive sense only and not for purposes of limitation.

That which is claimed:

1. An adaptor connecting a source of primary gas to an endoscopic device, the adaptor comprising an adaptor body having: a first fluid transport component in a non-fluid connection with a second fluid transport component, the first and second fluid transport components each having walls with tubular exterior surfaces and interior surfaces defining respective first and second channels extending therethrough, each fluid transport component having a flared open end, a tapered open end, and a central body between the flared open end and the tapered open end; wherein the tubular exterior surfaces of the first and second fluid transport components are attached to each other at an end of the flared open ends and contiguous along an entire length of the second fluid transport flared open end, and the tubular exterior surfaces are separated at the tapered open end and at least a portion of the central body, wherein the channel in the first fluid transport component is a linear liquid channel, and the channel in the second fluid transport component is a linear gas channel in fluid connection with the source of primary gas; and a tubular inlet port extending outward from the tubular exterior surface of the central body of the second fluid transport component such that the walls of the adapter form one linear channel and one branched channel, wherein the tubular inlet portion includes a central gas passage in direct fluid connection with the gas channel formed in the second fluid transport component, wherein a secondary gas is provided through the central gas passage to the gas channel in lieu of or in addition to the primary gas, wherein the tubular inlet port and the central gas passage thereof are substantially perpendicular to a respective one of the first or second channels, wherein a first engagement portion is defined by the flared open ends of both the first and second fluid transport components, a second engagement portion is defined by the tapered open ends of both the first and second fluid transport components, the first engagement portion is engageable with a configuration and a size that are the same as the second engagement portion.

2. The adaptor of claim 1, further comprising a sealing member located at the interior surface of one or both of the flared open ends of the first and second fluid transport components.

3. The adaptor of claim 1, wherein the tubular inlet port is substantially perpendicular to the exterior surface of the respective one of the first or second fluid transport components.

4. The adaptor of claim 1, wherein the adaptor body is a single, monolithic structure.

5. The adaptor of claim 1, wherein the internal diameter of the gas channel at the tapered open end of the channel is greater than the internal diameter of the liquid channel at the tapered open end of the channel.

6. The adaptor of claim 1, wherein the external diameter of the flared open end of the first fluid transport component is greater than the external diameter of the flared open end of the second fluid transport component.

7. The adaptor of claim 1, wherein the flared open ends of the first and second fluid transport components are shaped to engage fluid transport elements extending from a portion of the endoscopic device.

8. The adaptor of claim 7, wherein the flared open ends are shaped to facilitate a press-fit, sealed engagement with the fluid transport elements on the endoscopic device without secondary engaging means.

9. The adaptor of claim 1, wherein the first and second fluid transport components are substantially parallel and are in a side-by-side connection.

10. The adaptor of claim 1, wherein the external diameter of the central body is greater than the external diameter of each of the tapered open ends of the first and second fluid transport components, and wherein the external diameter of the central body is less than the external diameter of each of the flared open ends of the first and second fluid transport components.

11. The adaptor of claim 1, wherein the external diameter of each of the flared open ends of the first and second fluid transport components is greater than the external diameter of each of the tapered open ends of the first and second fluid transport components.

12. The adaptor of claim 1, wherein the tapered open end of the first or second transport components comprises a metallic material, and wherein the remaining portion of the adaptor body comprises a polymeric material.

13. The adaptor of claim 1, further comprising a shroud extending radially outwardly from the exterior surfaces of the first and second fluid transport components, the shroud further extending axially with respect to the first and second fluid transport components so as to at least partially surround the tapered open end of the first and/or second fluid transport component.

14. The adapter of claim 13, wherein the shroud comprises a wall extending circumferentially about the first and second fluid transport components so as to define an opening for at least partially receiving the tapered open end of the first and/or second fluid transport component.

15. The adaptor of claim 13, wherein the shroud extends axially such that the tapered open end of the second fluid transport component is completely surrounded by the shroud, and wherein the tapered open end of the first fluid transport component is not completely surrounded by the shroud; and wherein the shroud is formed of a different material than the adapter body.

16. An adaptor connecting a source of primary gas to an endoscopic device, the adaptor comprising an adaptor body having: a first fluid transport component in a non-fluid connection with a second fluid transport component, the first and second fluid transport components each having walls with exterior surfaces and interior surfaces defining respective first and second channels extending therethrough, each fluid transport component having a flared open end, a tapered open end, and a central body between the flared open end and the tapered open end; wherein the exterior surfaces of the first and second fluid transport components are attached to each other at an end of the flared open ends and contiguous along an entire length of the second fluid transport flared open end, and the exterior surfaces are separated at the tapered open end and at least a portion of the central body, wherein the channel in the first fluid transport component is a liquid channel, and the channel in the second fluid transport component is a gas channel in fluid connection with the source of primary gas; and a tubular inlet port extending outward from the exterior surface of the first or second fluid transport component such that the walls of the adapter form one linear channel and one branched channel, wherein the tubular inlet portion includes a central gas passage in fluid connection with the channel formed in the second fluid transport component, wherein a secondary gas is provided through the gas passage to the gas channel in lieu of or in addition to the primary gas, and wherein a first engagement portion is defined by the flared open ends of both the first and the second fluid transport components, a second engagement portion is defined by the tapered open ends of both the first and second fluid transport components, the first engagement portion is engageable with a configuration and a size that are the same as the second engagement portion; and a shroud extending radially outwardly from the exterior surfaces of the first and second fluid transport components, the shroud further extending axially with respect to the first and second fluid transport components so as to at least partially surround the tapered open end of the first and/or second fluid transport component; and wherein one or more of the shroud, tubular inlet port, first fluid transport component, or second fluid transport component is formed of the same material as the adaptor body.

17. The adaptor of claim 16, further comprising a sealing member located at the interior surface of one or both of the flared ends of the first and second fluid transport components.

18. The adaptor of claim 1, wherein the tubular inlet port extending from outward from the tubular exterior surface of the first or second fluid transport component comprises a female port.

19. The adaptor of claim 16, wherein the tubular inlet port extending from outward from the tubular exterior surface of the first or second fluid transport component comprises a female port.

20. The adaptor of claim 1, wherein inner and outer diameters of the central body of each fluid transport component are smaller than inner and outer diameters of the respective flared open end, and larger than inner and outer diameters of the respective tapered open end.

21. The adaptor of claim 16, wherein inner and outer diameters of the central body of each fluid transport component are smaller than inner and outer diameters of the respective flared open end, and larger than inner and outer diameters of the respective tapered open end.

* * * * *